US009079899B2

(12) United States Patent
Chen et al.

(10) Patent No.: US 9,079,899 B2
(45) Date of Patent: Jul. 14, 2015

(54) ANTI-STAPHYLOCOCCAL CELECOXIB DERIVATIVES

(75) Inventors: Ching-Shih Chen, Upper Arlington, OH (US); Hao-Chieh Chiu, Sanchohng (TW); Dasheng Wang, Dublin, OH (US); Samuel K. Kulp, Hilliard, OH (US)

(73) Assignee: THE OHIO STATE UNIVERSITY, Columbus, OH (US)

( * ) Notice: Subject to any disclaimer, the term of this patent is extended or adjusted under 35 U.S.C. 154(b) by 188 days.

(21) Appl. No.: 13/882,897

(22) PCT Filed: Oct. 31, 2011

(86) PCT No.: PCT/US2011/058501
§ 371 (c)(1), (2), (4) Date: Jul. 17, 2013

(87) PCT Pub. No.: WO2012/061260
PCT Pub. Date: May 10, 2012

(65) Prior Publication Data
US 2013/0289004 A1 Oct. 31, 2013

Related U.S. Application Data

(60) Provisional application No. 61/408,680, filed on Nov. 1, 2010.

(51) Int. Cl.

| | |
|---|---|
| *A61K 31/415* | (2006.01) |
| *A61K 31/5415* | (2006.01) |
| *C07D 471/04* | (2006.01) |
| *C07D 231/12* | (2006.01) |
| *C07D 405/04* | (2006.01) |

(52) U.S. Cl.
CPC ............ *C07D 471/04* (2013.01); *A61K 31/415* (2013.01); *A61K 31/5415* (2013.01); *C07D 231/12* (2013.01); *C07D 405/04* (2013.01)

(58) Field of Classification Search
None
See application file for complete search history.

(56) References Cited

U.S. PATENT DOCUMENTS

| | | | | |
|---|---|---|---|---|
| 5,521,207 | A | 5/1996 | Graneto | |
| 5,760,068 | A | 6/1998 | Talley et al. | |
| 6,136,839 | A | 10/2000 | Isakson et al. | |
| 8,039,502 | B2 * | 10/2011 | Chen et al. .................... | 514/406 |
| 2006/0079566 | A1 * | 4/2006 | Chen ............................ | 514/406 |
| 2009/0111799 | A1 | 4/2009 | Chen et al. | |

FOREIGN PATENT DOCUMENTS

EP 2246332 A1 3/2010

OTHER PUBLICATIONS

Wang et al., "Synthesis and Anti-Microbial Activity of Some New Fluorinated 1H-Pyrazoles" Journal of Fluorine Chemistry, vol. 131, 2010, pp. 584-586.
Faidallah, et al., "Synthesis and Biological Evaluation of new 3-Trifluoromethylpyrazolesulfonyl-Urea and Thiourea Derivatives as Antidiabetic and Antimicrobial Agents" Journal of Fluorine Chemistry, vol. 132, 2011, pp. 131-137.

Chiu et al. "Pharmacological Exploitation of an Off-Target Antibacterial Effect of the Cyclooxygenase-2 Inhibitor Celecoxib against *Franscisella tularensis*" Antimicrobial Agents and Chemotherapy, American Society for Microbiology, vol. 53, No. 7, 2009, pp. 2998-3002.

Zhu et al., "Using Cyclooxygenase-2 Inhibitors as Molecular Platforms to Develop a New Class of Apoptosis-Inducing Agents" Journal of National Cancer Institute, vol. 94, No. 24, 2004, pp. 1745-1757.

Chiu et al., "Eradication of Intracellular *Salmonella enterica* Serovar Typhimurium with a Small-Molecule, Host Cell-Directed Agent" Antimicrobial Agents and Chemotherapy, vol. 53, No. 12, 2009, pp. 5236-5244.

Database Registry [online] Chemical Abstracts Service, Columbus, OH, US, Nov. 26, 2007, XP002724515, retrieved from SNT accession No. 955963-00-5, Database accession No. 955963-00-5 abstract.

Kalle et al., "Inhibition of Bacterial Multidrug Resistance by Celecoxib, a Cyclooygenase-2 Inhibitor" Antimicrobial Agents and Chemotherapy, vol. 55, No. 1, 2010, pp. 439-442.

Kane, Jr. et al., "Ureas of 5-Aminopyrazole and 2-Aminotiazole Inhibit Growth of Gram-Positive Bacteria" Bioorganic & Medicinal Chemistry Letters, vol. 13, 2003, pp. 4463-4466.

* cited by examiner

*Primary Examiner* — Kamal Saeed
(74) *Attorney, Agent, or Firm* — Tarolli, Sundheim, Covell & Tummino LLP

(57) ABSTRACT

A method of treating infection by *Staphylococcus* in a subject by administering a pharmaceutical composition including a celecoxib derivative of formula I or a Formula I pharmaceutically acceptable salt thereof is described. The preparation of numerous celecoxib derivatives for testing as potential anti-staphylococcal agents is also described.

11 Claims, 3 Drawing Sheets

ANTI-STAPHYLOCOCCAL CELECOXIB DERIVATIVES

RELATED APPLICATIONS

This application claims the benefit of provisional U.S. patent application Ser. No. 61/408,680 filed on Nov. 1, 2010 for ANTI-*STAPHYLOCOCCAL* CELECOXIB DERIVATIVES, the entire disclosure of which is fully incorporated herein by reference.

GOVERNMENT FUNDING

The present invention was supported by Award Number UL1RR025755 from the National Center for Research Resources, funded by the Office of the Director, National Institutes of Health (OD) and supported by the NTH Roadmap for Medical Research. The Government has certain rights in this invention.

BACKGROUND

*Staphylococcus aureus*, a gram-positive bacterium, is one of the leading causes of hospital- and community-acquired infections in developed countries. It is estimated that *S. aureus* is commensally associated with skin, skin glands and mucous membranes of 20-30% of the human population. *S. aureus* can cause infection of the bloodstream, lower respiratory track, skin and soft tissue, leading to bacteremia, pneumonia, endocarditis and osteomyelitis. Initially, *S. aureus* infections could be successfully treated with β-lactam antibiotics, like penicillin and methicillin. However, by the mid-1900s, the emergence of resistant strains of *S aureus* had been reported, including methicillin-resistant *S. aureus* (MRSA) which has become endemic in many hospitals worldwide. Kirby, W. M., Science 99, 452-3 (1944). In addition to β-lactam antibiotics, *S. aureus* has also developed resistance to several other classes of antibiotics, including aminoglycosides, macrolides, lincosamides, chloramphenicol, sulfonamides, streptomycin and tetracycline. Schito, G. C., Cli. Microbiol Infect 12 Suppl 1, 3-8 (2006). The capability of *S. aureus* to resist multiple antibiotics has rendered its treatment difficult, leading to a higher mortality in patients. Thus, development of new antibacterial agents effective against *S. aureus*, especially strains resistant to multiple antibiotics, has become an urgent public health issue.

SUMMARY OF THE INVENTION

*Staphylococcus aureus* is an important gram-positive pathogen, which has developed multi-drug resistance causing serious clinical challenges to successful therapy. Herein, the inventors demonstrate that the cyclooxygenase-2 (COX-2) inhibitor celecoxib exhibits significant inhibitory activity against a variety of *Staphylococcus* species, including *Staphylococcus aureus, Staphylococcus epidermidis* and methicillin-resistant *Staphylococcus aureus* (MRSA) directly in growth medium that is independent of its COX-2-inhibitory activity. By screening against a celecoxib-based focused compound library, the inventors identified two agents, compounds 36 and 46, which showed particularly potent anti-*Staphylococcus* activities without acute cytotoxicity against human cancer cells. Evidence indicates that compounds 36 and 46 are bacteriostatic agents capable of suppressing the growth of a broad range of *Staphylococcus* species with similar potencies irrespective of multi-antibiotic-resistant phenotype. This finding suggests that the mode of action of these two compounds is distinct from those of existing antibiotics.

Accordingly, one aspect of the invention provides a method of treating infection by *Staphylococcus* in a subject that includes administering to the subject a pharmaceutical composition including a compound of formula I or a pharmaceutically acceptable salt thereof:

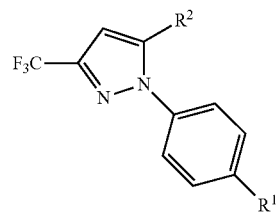

I wherein $R^1$ is selected from carboxamide, sulfonamide, amino, aminosulfonamide, and acylamido groups, and $R^2$ is selected from aryl, aralkyl, fused aryl groups, and fused heteroaryl groups. The method can be used to treat various types of *Staphylococcus* infection, including *Staphylococcus* that is methicillin-resistant, *Staphylococcus aureus*, and *Staphylococcus aureus* that is methicillin-resistant.

Another aspect of the invention provides a variety of pyrazole compounds of the following formula:

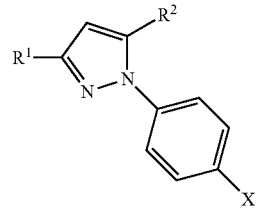

wherein X is selected from the group consisting of methanesulfonamide, aminosulfonamide, carboxamide and urea, $R^1$ is a methyl or trifluoromethyl moiety, and $R^2$ is an aryl group selected from the group consisting of substituted and unsubstituted phenyl, biphenyl, naphthyl, anthracenyl, and phenanthrenyl groups.

In further embodiments, $R^2$ of the pyrazole compounds can be an aryl group selected from the group consisting of:

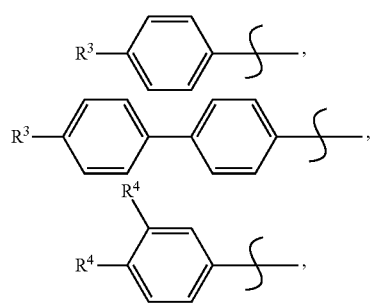

mono-methyl substituted naphthyl, and unsubstituted naphthyl, anthracenyl, and phenanthrenyl groups, wherein $R^3$ is selected from the group consisting of hydrogen, chloro, fluoro, bromo, methyl, trifluoromethyl, methoxy, cyano, nitro, amino, and carboxamide moieties, and wherein $R^4$ is selected from the group consisting of methyl, methoxy, chloro, and fluoro moieties.

DETAILED DESCRIPTION OF THE INVENTION

Figure 1:
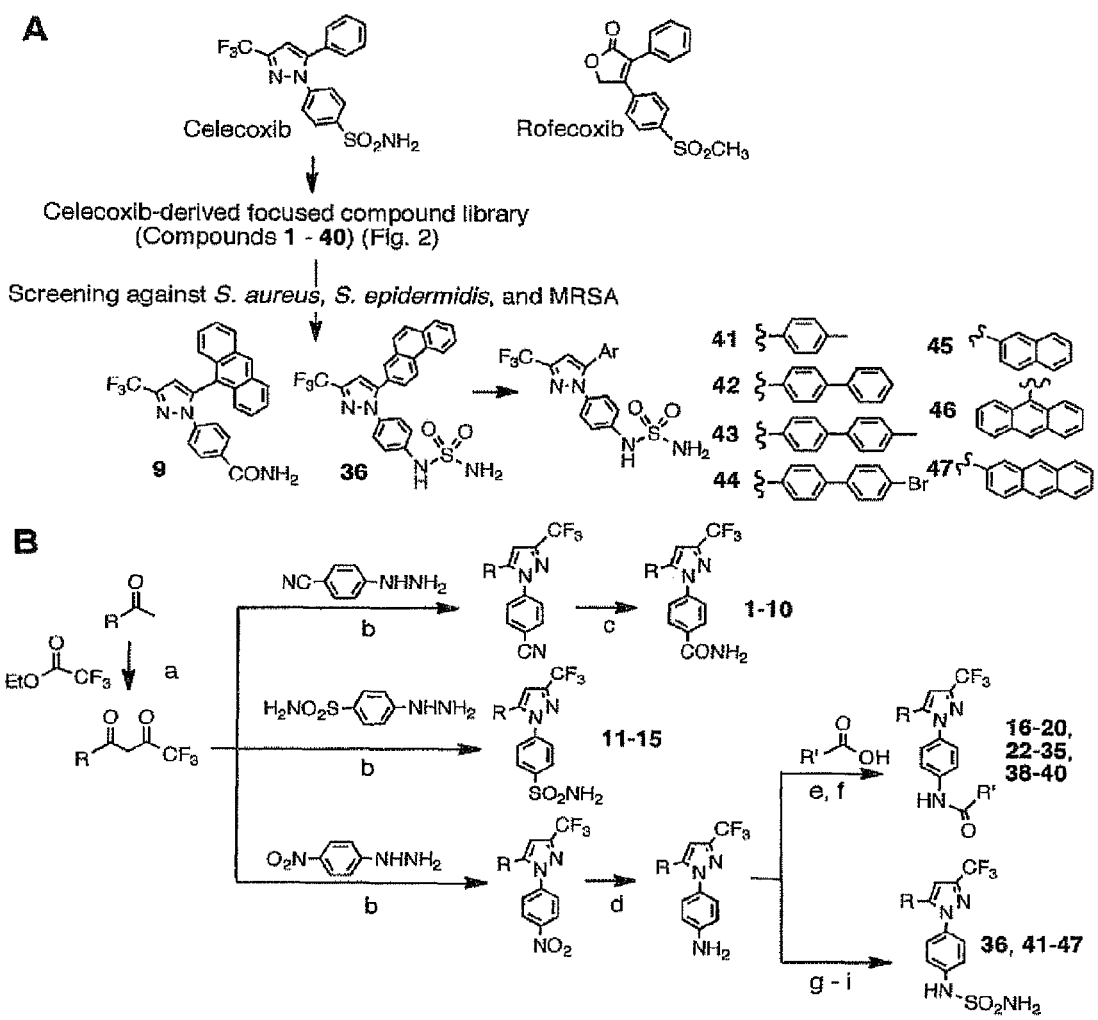
FIG. 1 provides a schematic representation of the screening of the celecoxib-based focused compound library for lead identification, followed by structural optimization, to identify lead anti-Staphylococcus agents. (B) General synthetic procedures for compounds 1-47. Reaction conditions: a, NaH, THF; b, HCl, EtOH, reflux; c, $Na_2CO_3$, $H_2O_2$; d, $PtO_2/H_2$, EtOH; e, EDC, THF, t-Boc-protected glycine, β-alanine, or D- or L-lysine; f, HCl, EtOAc; g, chlorosulfonyl isocyanate, t-BuOH, $CH_2Cl_2$; h, triethylamine, $CH_2Cl_2$; i, trifluoroacetic acid, $CH_2Cl_2$.

The inventors have demonstrated herein that celecoxib directly suppresses the growth of Staphylococcus species, including S. aureus, S. epidermidis and MRSA, while the generally more potent COX-2 inhibitor rofecoxib was ineffective. This dissociation of the anti-Staphylococcus effect of celecoxib from its COX-2 inhibitory activity provided a basis for the pharmacological exploitation of celecoxib to develop novel agents for the treatment of MRSA. Thus, using celecoxib as a scaffold, the inventors developed a focused compound library, the screening of which led to the identification of compounds 36 and 46, which exhibit relatively high anti-Staphylococcus potencies without acute cytotoxicity against human cells.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for celecoxib derivatives of this invention are those that do not interfere with the anti-Staphylococcal activity of the celecoxib derivatives. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alley groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and substituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "fused aryl group" includes fused carbocyclic aromatic rings or ring systems. Fused aryl groups include a plurality of aromatic rings that are fused to form a single aromatic system. Examples of fused aryl groups include naphthalene ($C_{10}$), anthracene ($C_{14}$), phenanthrene ($C_{14}$) and pyrene ($C_{16}$) fused aryl groups. Collectively, fused aryl groups can be referred to by reference to the number of carbon ring atoms they contain; i.e., a $C_{10}$-$C_{18}$ carboaryl group.

The term "fused heteroaryl group" refers to fused aromatic ring systems including a plurality of aromatic rings that are fused to form a single aromatic system, in which one or more of the aromatic rings is a heteroaromatic ring. Fused heteroaryl groups are otherwise like fused aryl groups. Examples of fused heteroaryl groups include benzofuran, isobenzofuran, benzothiopene, indole, isoindole, $C_{10}$ heteroaryl groups derived from quinoline, isoquinoline, benodiazine, pyridopyridine, and $C_{14}$ heteroaryl groups derived from acridine and xanthenes.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the substituted group and that group with one or more nonperoxidic O, N, S, or F substituents or other conventional substituents such as methyl groups. Where the term "moiety" is used to describe a chemical compound or substituent, only an substituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Additional substituents that can optionally be substituted on a group are further defined below.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amino groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$.

Amino: —NR$^1$R$^2$, wherein R$^1$ and R$^2$ are independently amino substituents, for example, hydrogen or a $C_{1-7}$ alkyl group. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino.

Acylamido (acylamino): —NR$^1$C(=O)R$^2$, wherein R$^1$ is an amide substituent, for example, hydrogen or a $C_{1-7}$ alkyl group. Examples of acrylamide groups include, but are not limited to, —NHC(=O)CH$_3$, —NHC(=O)CH$_2$CH$_3$, and —NHC(=O)Ph. Acylamido groups can be substituted; for example, the acylamido groups can be amine substituted acylamido groups having the formula —NH—CO—(CH$_2$)$_x$—NH$_2$, wherein x is an integer from 1-4.

Ureido: —N(R$^1$)CONR$^2$R$^3$ wherein R$^2$ and R$^3$ are independently amino substituents, as defined for amino groups, and R$^1$ is a ureido substituent, for example, hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Sulfonyl (sulfone): —S(=O)$_2$R, wherein R is a sulfone substituent, for example, a $C_{1-7}$ alkyl group or a $C_{5-20}$ aryl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl). The sulfone substituent may in some cases be an amino group, as defined above. These groups may be termed "aminosulfonyl" groups.

Sulfonamino: —NR$^1$S(=O)$_2$R, wherein R$^1$ is an amino substituent, as defined for amino groups, and R is a sulfonamino substituent, for example, a $C_{1-7}$ alkyl group or a $C_{5-20}$ aryl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term celecoxib derivatives, as used herein, is a shorthand for the celecoxib compounds of the invention, as described by the formulas provided herein; and is not meant to encompass all possible compounds that might be characterized as being based on the celecoxib scaffold by one skilled in the art.

Treat", "treating", and "treatment", etc., as used herein, refer to any action providing a benefit to a subject afflicted with a condition or disease such as a *Staphylococcus* infection, including improvement in the condition through lessening or suppression of at least one symptom, delay in progression of the disease, prevention or delay in the onset of the disease, etc.

Prevention, as used herein, refers to any action providing a benefit to a subject at risk of being afflicted with a condition or disease such as *Staphylococcus* infection, including avoidance of infection or a decrease of one or more symptoms of the disease should infection occur. The subject may be at risk due to exposure to *Staphylococcus aureus*, as a result of, for example, being in a hospital environment.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The present invention provides methods for treating or preventing infection by *Staphylococcus* in a subject by administering a celecoxib derivative. The structure of celecoxib derivatives 1-47 is shown in FIG. 1. In one embodiment, the invention provides a method of treating infection by *Staphylococcus* in a subject that includes administering to the subject a pharmaceutical composition including a compound of formula I or a pharmaceutically acceptable salt thereof:

I wherein $R^1$ is selected from carboxamide, sulfonamide, amino, aminosulfonamide, and acylamido groups, and $R^2$ is selected from aryl, aralkyl, fused aryl groups, and fused heteroaryl groups. In a further embodiment of this method, $R^1$ is carboxamide and $R^2$ is:

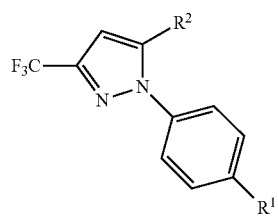

In yet another embodiment of the invention, the compound of formula I is compound 9 (4-(5-Anthracen-9-yl-3-trifluoromethyl-pyrazol-1-yl)-benzamide) and has the structure:

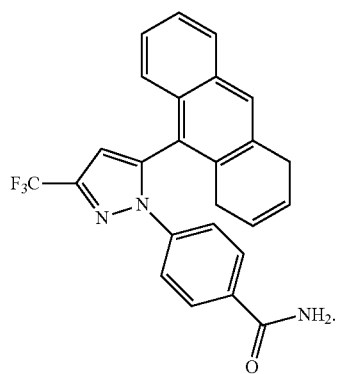 [SMILES: NC(=O)c1ccc(-n2nc(C(F)(F)F)cc2-c2c3c(cc4ccccc24)CC=CC3)cc1]

The celecoxib derivative of formula I can also include substituents such that $R^1$ is sulfonamide and $R^2$ is selected from the group consisting of:

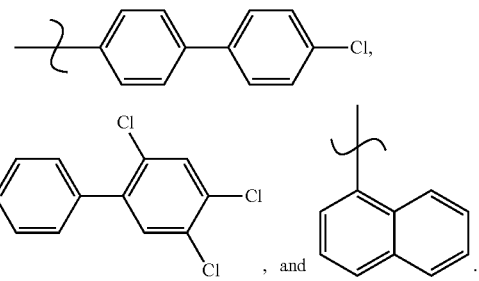

Alternately, the celecoxib derivative of formula I can include substituents such that $R^1$ is acylamido and $R^2$ is selected from the group consisting of:

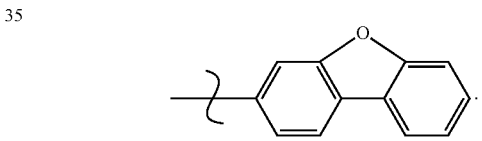

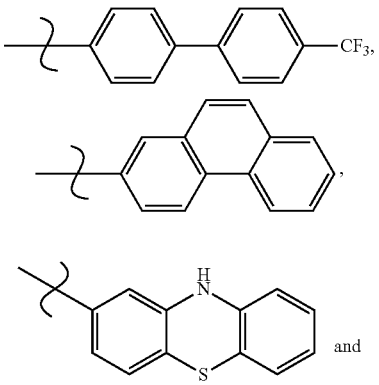

In embodiments of the method where the structures shown above are used, the acylamido can further be defined as an amine substituted acylamido having the structure $-NH-CO-(CH_2)_x-NH_2$, wherein x is an integer from 1-4.

Alternately, the celecoxib derivative of formula I can include substituents such that $R^1$ is aminosulfonamide, and $R^2$ is a phenyl, biphenyl, naphthyl, or anthracenyl group. In further embodiments, these derivatives can be compounds of formula I having the structure:

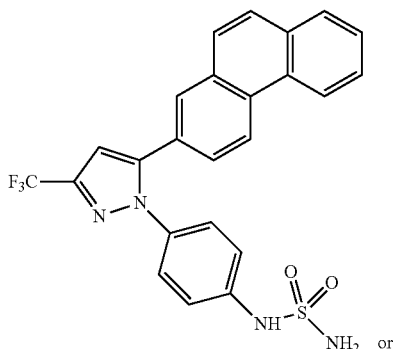

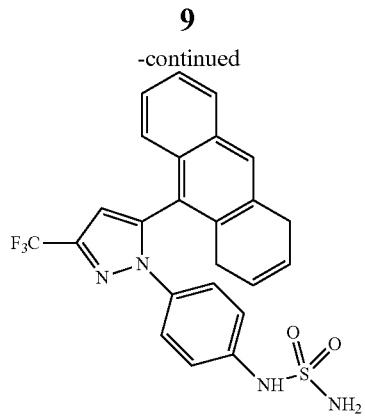

Which are compound 36 (N-[4-(5-Phenanthren-2-yl-3-trifluoromethyl-pyrazol-1-yl)-phenyl]-aminosulfonamide) and compound 46 (N-[4-(5-Anthracen-yl-3-trifluoromethyl-pyrazol-1-yl)-phenyl]-aminosulfonamide) respectively.

The methods of treating or preventing *Staphylococcus* infection using the compounds described above can also be used to treat or prevent particular types of *Staphylococcus* infection. For example, in one embodiment, the method can be used to treat or prevent infection by *Staphylococcus* that are methicillin-resistant. In other embodiments, the celecoxib derivatives can be used to treat or prevent *Staphylococcus* infections by specific species of *Staphylococcus*. Examples of species that can be treated include *S. aureus*, and *S. epidermidis*, *S. haemolyticus*, *S. hominis*, *S. intermedius*, *S. saprophyticus*, and *S. lugdunesis*. In particular, the celecoxib derivatives can be used to treat or prevent infection by *Staphylococcus aureus*, or *Staphylococcus aureus* that is methicillin-resistant.

In another aspect of the invention, a wide variety of celecoxib derivatives have been prepared. General methods for preparing these compounds are described herein. For example, one embodiment of the invention includes pyrazole compounds of formula II:

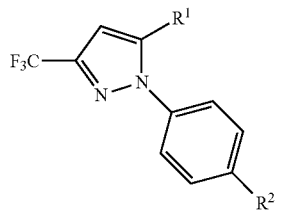

wherein $R^1$ is a substituted or unsubstituted biphenyl, fused aryl, or fused heteroaryl group, $R^2$ is aminosulfonamide or an amine-substituted acylamido having the structure —NH—CO—(CH$_2$)$_x$—NH$_2$, x is an integer from 2-4, and pharmaceutically acceptable salts thereof.

In an additional embodiment, the pyrazole compounds of formula II can include $R^1$ that is selected from the group consisting of:

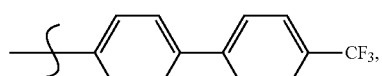

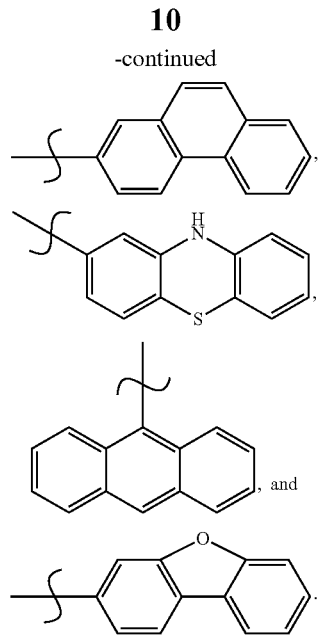

These groups are trifluoromethyl biphenyl, phenanthrenyl, phenothiazine, anthracenyl, and dibenzo[b,d]furanyl groups, respectively.

In particular, the compounds of formula II include the following compound when $R^1$ is a phenanthrenyl or anthracenyl group:

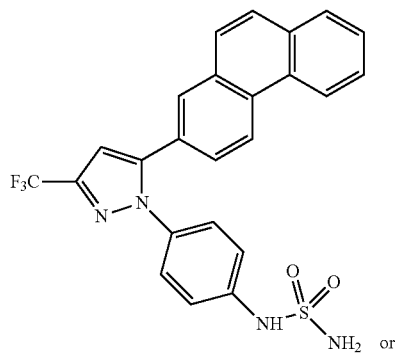

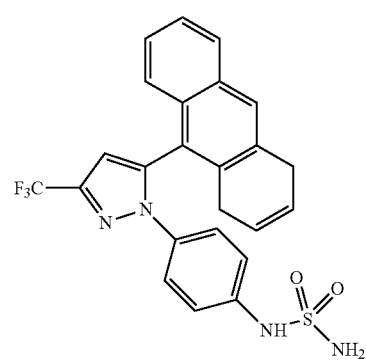

or a pharmaceutically acceptable salt thereof.

In another aspect, the compounds of the present invention include the pyrazole compounds of formula III:

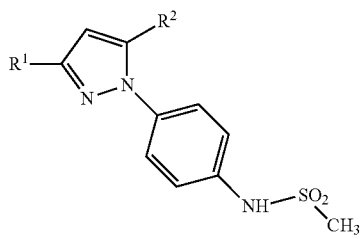

III wherein $R^1$ is a methyl or trifluoromethyl moiety $R^2$ is an aryl group selected from the group consisting of substituted and unsubstituted phenyl, biphenyl, naphthyl, anthracenyl, and phenanthrenyl groups.

In some embodiments, the compounds of formula III can include $R^2$ as an aryl group selected from the group consisting of:

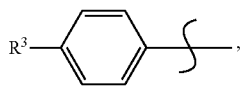

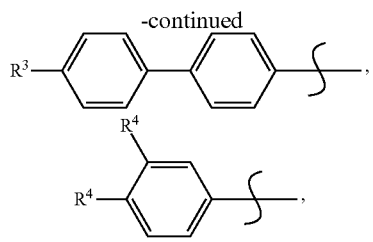

mono-methyl substituted naphthyl, and unsubstituted naphthyl, anthracenyl, and phenanthrenyl groups, wherein $R^3$ is selected from the group consisting of hydrogen, chloro, fluoro, bromo, methyl, trifluoromethyl, methoxy, cyano, nitro, amino, and carboxamide moieties, and wherein $R^4$ is selected from the group consisting of methyl, methoxy, chloro, and fluoro moieties. A mono-methyl substituted naphthyl group, as defined herein, is a naphthyl group that includes a single methyl substituent attached to the naphthyl group, such as 4-methyl naphthalene.

Separate embodiments of the compounds of formula III can include $R^1$ as either a methyl or trifluoromethyl substituent.

Specific examples of compounds according to formula III in which $R^1$ is methyl are shown in Table I, in which $R^2$ is shown as the Ar group.

TABLE I

Celecoxib Derivatives based on Formula III

| Ar | Name |
|---|---|
| (phenyl) | N-[4-(3-Methyl-5-phenyl-pyrazol-1-yl)-phenyl]-methanesulfonamide |
| H₃C-phenyl | N-[4-(5-p-Tolyl-3-methyl-pyrazol-1-yl)-phenyl]-methanesulfonamide |
| H₃CO-phenyl | N-{4-[5-(4-Methoxy-phenyl)-3-methyl-pyrazol-1-yl]-phenyl}-methanesulfonamide |
| F₃C-phenyl | N-{4-[3-Methyl-5-(4-methyl-phenyl)-pyrazol-1-yl]-phenyl}-methanesulfonamide |
| Cl-phenyl | N-{4-[5-(4-Chloro-phenyl)-3-methyl-pyrazol-1-yl]-phenyl}-methanesulfonamide |
| F-phenyl | N-{4-[5-(4-Fluoro-phenyl)-3-methyl-pyrazol-1-yl]-phenyl}-methanesulfonamide |
| NC-phenyl | N-{4-[5-(4-Cyano-phenyl)-3-methyl-pyrazol-1-yl]-phenyl}-methanesulfonamide |
| O₂N-phenyl | N-{4-[5-(4-Nitro-phenyl)-3-methyl-pyrazol-1-yl]-phenyl}-methanesulfonamide |

TABLE I-continued

Celecoxib Derivatives based on Formula III

| Ar | Name |
|---|---|
| H₂N–⌬– | N-{4-[5-(4-Amino-phenyl)-3-methyl-pyrazol-1-yl]-phenyl}-methanesulfonamide |
| H₂NOC–⌬– | 4-[2-(4-Methanesulfonylamino-phenyl)-5-methyl-2H-pyrazol-3-yl]-benzamide |
| 3,4-(H₃C)₂–⌬– | N-{4-[5-(3,4-Dimethyl-phenyl)-3-methyl-pyrazol-1-yl]-phenyl}-methanesulfonamide |
| 3,4-(H₃CO)₂–⌬– | N-{4-[5-(3,4-Dimethoxy-phenyl)-3-methyl-pyrazol-1-yl]-phenyl}-methanesulfonamide |
| 3,4-Cl₂–⌬– | N-{4-[5-(3,4-Dichloro-phenyl)-3-methyl-pyrazol-1-yl]-phenyl}-methanesulfona |
| 3,4-F₂–⌬– | N-{4-[5-(3,4-Difluoro-phenyl)-3-methyl-pyrazol-1-yl]-phenyl}-methanesulfona |
| Ph–⌬–⌬– | N-[4-(5-Biphenyl-4-yl-3-methyl-pyrazol-1-yl)-phenyl]-methanesulfonamide |
| Cl–⌬–⌬– | N-{4-[5-(4'-Chloro-biphenyl-4-yl)-3-methyl-pyrazol-1-yl]-phenyl}-methanesulfonamide |
| F–⌬–⌬– | N-{4-[5-(4'-Fluoro-biphenyl-4-yl)-3-methyl-pyrazol-1-yl]-phenyl}-methanesulfonamide |
| Br–⌬–⌬– | N-{4-[5-(4'-Bromo-biphenyl-4-yl)-3-methyl-pyrazol-1-yl]-phenyl}-methanesulfonamide |
| H₃C–⌬–⌬– | N-{4-[5-(4'-Methyl-biphenyl-4-yl)-3-methyl]-pyrazol-1-yl]-phenyl}-methanesulfonamide |
| F₃C–⌬–⌬– | N-{4-[5-(4'-Methyl-biphenyl-4-yl)-3-methyl-pyrazol-1-yl]-phenyl}-methanesulfonamide |
| MeO–⌬–⌬– | N-{4-[5-(4'-Methoxy-biphenyl-4-yl)-3-methyl-pyrazol-1-yl]-phenyl}-methanesulfonamide |
| NC–⌬–⌬– | N-{4-[5-(4'-Cyano-biphenyl-4-yl)-3-methyl-pyrazol-1-yl]-phenyl}-methanesulfonamide |

TABLE I-continued

Celecoxib Derivatives based on Formula III

| Ar | Name |
|---|---|
| 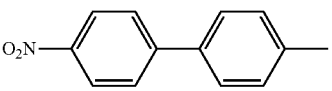 | N-{4-[5-(4'-Nitro-biphenyl-4-yl)-3-methyl-pyrazol-1-yl]-phenyl}-methanesulfonamide |
| 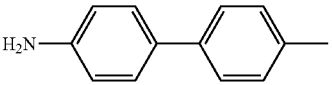 | N-{4-[5-(4'-Amino-biphenyl-4-yl)-3-methyl-pyrazol-1-yl]-phenyl}-methanesulfonamide |
| 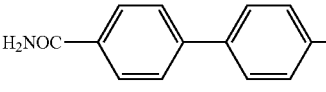 | 4'-[2-(4-Methanesulfonylamino-phenyl)-5-methyl-2H-pyrazol-3-yl]-biphenyl-4-carboxylic acid amide |
| 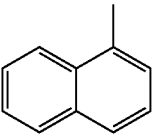 | N-[4-(5-Naphthalen-1-yl-3-methyl-pyrazol-1-yl)-phenyl]-methanesulfonamide |
| 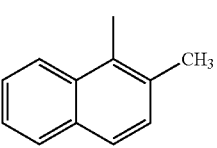 | N-{4-[5-(2-Methyl-naphthalen-1-yl)-3-methyl-pyrazol-1-yl]-phenyl}-methanesulfonamide |
| 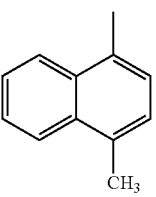 | N-{4-[5-(4-Methyl-naphthalen-1-yl)-3-methyl-pyrazol-1-yl]-phenyl}-methanesulfonamide |
| 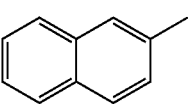 | N-[4-(5-Naphthalen-2-yl-3-methyl-pyrazol-1-yl)-phenyl]-methanesulfonamide |
| 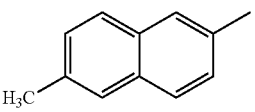 | N-{4-[5-(6-Methyl-naphthalen-2-yl)-3-methyl-pyrazol-1-yl]-phenyl}-methanesulfonamide |
| 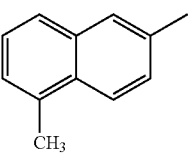 | N-{4-[5-(5-Methyl-naphthalen-2-yl)-3-methyl-pyrazol-1-yl]-phenyl}-methanesulfonamide |
| 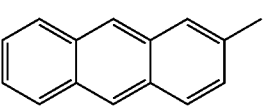 | N-[4-(5-Anthracen-2-yl-3-methyl-pyrazol-1-yl)-phenyl]-methanesulfonamide |
| 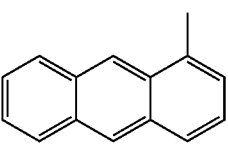 | N-[4-(5-Anthracen-1-yl-3-methyl-pyrazol-1-yl)-phenyl]-methanesulfonamide |

TABLE I-continued

Celecoxib Derivatives based on Formula III

| Ar | Name |
|---|---|
| (9-methylanthracene) | N-[4-(5-Anthracen-9-yl-3-methyl-pyrazol-1-yl)-phenyl]-methanesulfonamide |
| (3-methylphenanthrene) | N-[4-(5-Phenanthren-3-yl-3-methyl-pyrazol-1-yl)-phenyl]-methanesulfonamide |
| (2-methylphenanthrene) | N-[4-(5-Phenanthren-2-yl-3-methyl-pyrazol-1-yl)-phenyl]-methanesulfonamide |
| (1-methylphenanthrene) | N-[4-(5-Phenanthren-1-yl-3-methyl-pyrazol-1-yl)-phenyl]-methanesulfonamide |
| (9-methyl-5,6-dihydrophenanthrene) | N-{4-[5-(5,6-Dihydro-phenanthren-9-yl)-3-methyl-pyrazol-yl]-phenyl}-methanesulfonamide |
| (4-methylphenanthrene) | N-[4-(5-Phenanthren-4-yl-3-methyl-pyrazol-1-yl)-phenyl]-methanesulfonamide |

Specific examples of compounds according to formula III in which $R^1$ is trifluormethyl are shown in Table II, in which $R^2$ is shown as the Ar group.

TABLE II

Celecoxib Derivatives based on Formula III

| Ar | Name |
|---|---|
| (phenyl) | N-[4-(5-Phenyl-3-trifluoromethyl-pyrazol-1-yl)-phenyl]-methanesulfonamide |
| H₃C—(p-tolyl) | N-[4-(5-p-Tolyl-3-trifluoromethyl-pyrazol-1-yl)-phenyl]-methanesulfonamide |
| H₃CO—(4-methoxyphenyl) | N-{4-[5-(4-Methoxy-phenyl)-3-trifluoromethyl-pyrazol-1-yl]-phenyl}-methanesulfonamide |

TABLE II-continued

Celecoxib Derivatives based on Formula III

| Ar | Name |
|---|---|
| F₃C-C₆H₄- | N-{4-[3-Trifluoromethyl-5-(4-trifluoromethyl-phenyl)-pyrazol-1-yl]-phenyl}-methanesulfonamide |
| Cl-C₆H₄- | N-{4-[5-(4-Chloro-phenyl)-3-trifluoromethyl-pyrazol-1-yl]-phenyl}-methanesulfonamide |
| F-C₆H₄- | N-{4-[5-(4-Fluoro-phenyl)-3-trifluoromethyl-pyrazol-1-yl]-phenyl}-methanesulfonamide |
| NC-C₆H₄- | N-{4-[5-(4-Cyano-phenyl)-3-trifluoromethyl-pyrazol-1-yl]-phenyl}-methanesulfonamide |
| O₂N-C₆H₄- | N-{4-[5-(4-Nitro-phenyl)-3-trifluoromethyl-pyrazol-1-yl]-phenyl}-methanesulfonamide |
| H₂N-C₆H₄- | N-{4-[5-(4-Amino-phenyl)-3-trifluoromethyl-pyrazol-1-yl]-phenyl}-methanesulfonamide |
| H₂NOC-C₆H₄- | 4-[2-(4-Methanesulfonylamino-phenyl)-5-trifluoromethyl-2H-pyrazol-3-yl]-benzamide |
| 3,4-(H₃C)₂-C₆H₃- | N-{4-[5-(3,4-Dimethyl-phenyl)-3-trifluoromethyl-pyrazol-1-yl]-phenyl}-methanesulfonamide |
| 3,4-(H₃CO)₂-C₆H₃- | N-{4-[5-(3,4-Dimethoxy-phenyl)-3-trifluoromethyl-pyrazol-1-yl]-phenyl}-methanesulfonamide |
| 3,4-Cl₂-C₆H₃- | N-{4-[5-(3,4-Dichloro-phenyl)-3-trifluoromethyl-pyrazol-1-yl]-phenyl}-methanesulfona |
| 3,4-F₂-C₆H₃- | N-{4-[5-(3,4-Dichloro-phenyl)-3-trifluoromethyl-pyrazol-1-yl]-phenyl}-methanesulfona |
| C₆H₅-C₆H₄- | N-[4-(5-Biphenyl-4-yl-3-trifluoromethyl-pyrazol-1-yl)-phenyl]-methanesulfonamide |
| 4-Cl-C₆H₄-C₆H₄- | N-{4-[5-(4'-Chloro-biphenyl-4-yl)-3-trifluoromethyl-pyrazol-1-yl]-phenyl}-methanesulfonamide |
| 4-F-C₆H₄-C₆H₄- | N-{4-[5-(4'-Chloro-biphenyl-4-yl)-3-trifluoromethyl-pyrazol-1-yl]-phenyl}-methanesulfonamide |

TABLE II-continued

Celecoxib Derivatives based on Formula III

| Ar | Name |
|---|---|
| 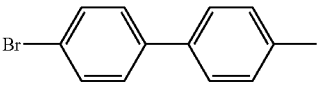 | N-{4-[5-(4'-Bromo-biphenyl-4-yl)-3-trifluoromethyl-pyrazol-1-yl]-phenyl}-methanesulfonamide |
| 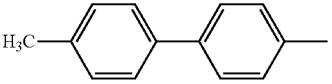 | N-{4-[5-(4'-Methyl-biphenyl-4-yl)-3-trifluoromethyl-pyrazol-1-yl]-phenyl}-methanesulfonamide |
| 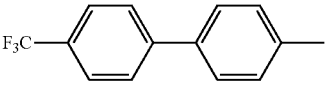 | N-{4-[5-(4'-Trifluoromethyl-biphenyl-4-yl)-3-trifluoromethyl-pyrazol-1-yl]-phenyl}-methanesulfonamide |
| 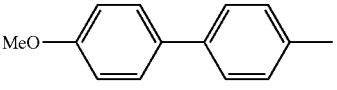 | N-{4-[5-(4'-Methoxy-biphenyl-4-yl)-3-trifluoromethyl-pyrazol-1-yl]-phenyl}-methanesulfonamide |
| 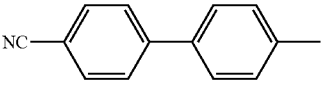 | N-{4-[5-(4'-Cyano-biphenyl-4-yl)-3-trifluoromethyl-pyrazol-1-yl]-phenyl}-methanesulfonamide |
| 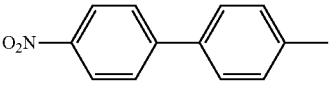 | N-{4-[5-(4'-Nitro-biphenyl-4-yl)-3-trifluoromethyl-pyrazol-1-yl]-phenyl}-methanesulfonamide |
| 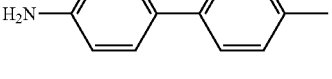 | N-{4-[5-(4'-Amino-biphenyl-4-yl)-3-trifluoromethyl-pyrazol-1-yl]-phenyl}-methanesulfonamide |
| 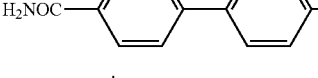 | 4'-[2-(4-Methanesulfonylamino-phenyl)-5-trifluoromethyl-2H-pyrazol-3-yl]-biphenyl-4-carboxylic acid amide |
| 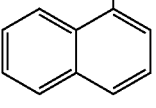 | N-[4-(5-Naphthalen-1-yl-3-trifluoromethyl-pyrazol-1-yl)-phenyl]-methanesulfonamide |
| 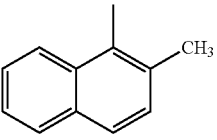 | N-{4-[5-(2-Methyl-naphthalen-1-yl)-3-trifluoromethyl-pyrazol-1-yl]-phenyl}-methanesulfonamide |
| 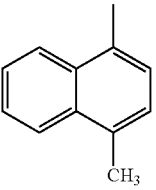 | N-{4-[5-(4-Methyl-naphthalen-1-yl)-3-trifluoromethyl-pyrazol-1-yl]-phenyl}-methanesulfonamide |
| 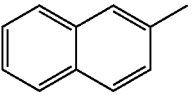 | N-[4-(5-Naphthalen-2-yl-3-trifluoromethyl-pyrazol-1-yl)-phenyl]-methanesulfonamide |
| 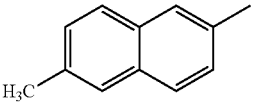 | N-{4-[5-(6-Methyl-naphthalen-2-yl)-3-trifluoromethyl-pyrazol-1-yl]-phenyl}-methanesulfonamide |

TABLE II-continued

Celecoxib Derivatives based on Formula III

| Ar | Name |
|---|---|
| 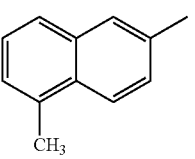 | N-{4-[5-(5-Methyl-naphthalen-2-yl)-3-trifluoromethyl-pyrazol-1-yl]-phenyl}-methanesul |
| 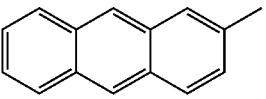 | N-[4-(5-Anthracen-2-yl-3-trifluoromethyl-pyrazol-1-yl)-phenyl]-methanesulfonamide |
| 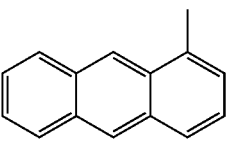 | N-[4-(5-Anthracen-1-yl-3-trifluoromethyl-pyrazol-1-yl)-phenyl]-methanesulfonamide |
| 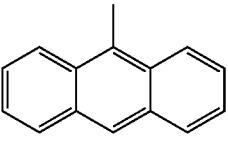 | N-[4-(5-Anthracen-9-yl-3-trifluoromethyl-pyrazol-1-yl)-phenyl]-methanesulfonamide |
| 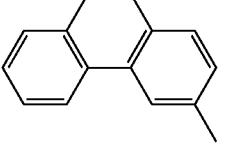 | N-[4-(5-Phenanthren-3-yl-3-trifluoromethyl-pyrazol-1-yl)-phenyl]-methanesulfonamide |
| 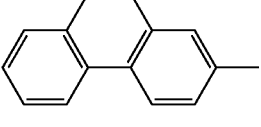 | N-[4-(5-Phenanthren-2-yl-3-trifluoromethyl-pyrazol-1-yl)-phenyl]-methanesulfonamide |
| 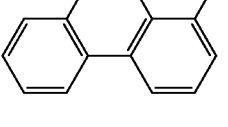 | N-[4-(5-Phenanthren-1-yl-3-trifluoromethyl-pyrazol-1-yl)-phenyl]-methanesulfonamide |
| 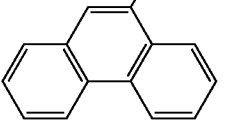 | N-{4-(5-(5,6-Dihydro-phenanthren-9-yl)-3-trifluoromethyl-pyrazol-1-yl]-phenyl}-methanesulfonamide |
| 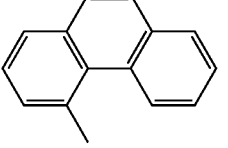 | N-[4-(5-Phenanthren-4-yl-3-trifluoromethyl-pyrazol-1-yl)-phenyl]-methanesulfonamide |

Another aspect of the invention provides pyrazole compounds of formula IV:

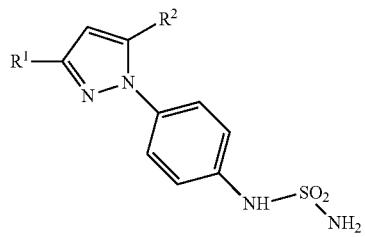

wherein $R^1$ is a methyl or trifluoromethyl moiety and $R^2$ is an aryl group selected from the group consisting of substituted and unsubstituted phenyl, biphenyl, naphthyl, anthracenyl, and phenanthrenyl groups.

In some embodiments, the compounds of formula IV can include $R^2$ as an aryl group selected from the group consisting of:

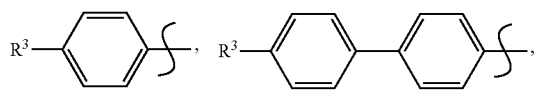

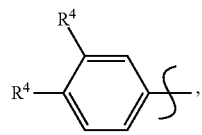

mono-methyl substituted naphthyl, and unsubstituted naphthyl, anthracenyl, and phenanthrenyl groups, wherein $R^3$ is selected from the group consisting of hydrogen, chloro, fluoro, bromo, methyl, trifluoromethyl, methoxy, cyano, nitro, amino, and carboxamide moieties, and wherein $R^4$ is selected from the group consisting of methyl, methoxy, chloro, and fluoro moieties.

Separate embodiments of the compounds of formula IV can include $R^1$ as either a methyl or trifluoromethyl substituent.

Specific examples of compounds according to formula IV in which $R^1$ is methyl are shown in Table III, in which $R^2$ is shown as the Ar group.

TABLE III

| Celecoxib Derivatives based on Formula IV | |
|---|---|
| Ar | Name |
| ⌬— | N-[4-(3-Methyl-5-phenyl-pyrazol-1-yl)-phenyl]-aminosulfonamide |
| H₃C—⌬— | N-[4-(5-p-Tolyl-3-methyl-pyrazol-1-yl)-phenyl]-aminosulfonamide |
| H₃CO—⌬— | N-{4-[5-(4-Methoxy-phenyl)-3-methyl-pyrazol-1-yl]-phenyl}-aminosulfonamide |
| F₃C—⌬— | N-{4-[3-Methyl-5-(4-methyl-phenyl)-pyrazol-1-yl]-phenyl}-aminosulfonamide |
| Cl—⌬— | N-{4-[5-(4-Chloro-phenyl)-3-methyl-pyrazol-1-yl]-phenyl}-aminosulfonamide |
| F—⌬— | N-{4-[5-(4-Fluoro-phenyl)-3-methyl-pyrazol-1-yl]-phenyl}-aminosulfonamide |
| NC—⌬— | N-{4-[5-(4-Cyano-phenyl)-3-methyl-pyrazol-1-yl]-phenyl}-aminosulfonamide |
| O₂N—⌬— | N-{4-[5-(4-Nitro-phenyl)-3-methyl-pyrazol-1-yl]-phenyl}-aminosulfonamide |

TABLE III-continued

Celecoxib Derivatives based on Formula IV

| Ar | Name |
|---|---|
| H₂N–C₆H₄– (4-amino-phenyl) | N-{4-[5-(4-Amino-phenyl)-3-methyl-pyrazol-1-yl]-phenyl}-aminosulfonamide |
| H₂NOC–C₆H₄– | 4-[2-(4-Aminosulfonylamino-phenyl)-5-methyl-2H-pyrazol-3-yl]-benzamide |
| 3,4-(H₃C)₂–C₆H₃– | N-{4-[5-(3,4-Dimethyl-phenyl)-3-methyl-pyrazol-1-yl]-phenyl}-aminosulfonamide |
| 3,4-(H₃CO)₂–C₆H₃– | N-{4-[5-(3,4-Dimethoxy-phenyl)-3-methyl-pyrazol-1-yl]-phenyl}-aminosulfonamide |
| 3,4-Cl₂–C₆H₃– | N-{4-[5-(3,4-Dichloro-phenyl)-3-methyl-pyrazol-1-yl]-phenyl}-aminosulfona |
| 3,4-F₂–C₆H₃– | N-{4-[5-(3,4-Difluoro-phenyl)-3-methyl-pyrazol-1-yl]-phenyl}-aminosulfona |
| biphenyl-4-yl | N-[4-(5-Biphenyl-4-yl-3-methyl-pyrazol-1-yl)-phenyl]-aminosulfonamide |
| 4'-Cl-biphenyl-4-yl | N-{4-[5-(4'-Chloro-biphenyl-4-yl)-3-methyl-pyrazol-1-yl]-phenyl}-aminosulfonamide |
| 4'-F-biphenyl-4-yl | N-{4-[5-(4'-Fluoro-biphenyl-4-yl)-3-methyl-pyrazol-1-yl]-phenyl}-aminosulfonamide |
| 4'-Br-biphenyl-4-yl | N-{4-[5-(4'-Bromo-biphenyl-4-yl)-3-methyl-pyrazol-1-yl]-phenyl}-aminosulfonamide |
| 4'-H₃C-biphenyl-4-yl | N-{4-[5-(4'-Methyl-biphenyl-4-yl)-3-methyl-pyrazol-1-yl]-phenyl}-aminosulfonamide |
| 4'-F₃C-biphenyl-4-yl | N-{4-[5-(4'-Methyl-biphenyl-4-yl)-3-methyl-pyrazol-1-yl]-phenyl}-aminosulfonamide |
| 4'-MeO-biphenyl-4-yl | N-{4-[5-(4'-Methoxy-biphenyl-4-yl)-3-methyl-pyrazol-1-yl]-phenyl}-aminosulfonamide |
| 4'-NC-biphenyl-4-yl | N-{4-[5-(4'-Cyano-biphenyl-4-yl)-3-methyl-pyrazol-1-yl]-phenyl}-aminosulfonamide |

TABLE III-continued

Celecoxib Derivatives based on Formula IV

| Ar | Name |
|---|---|
| 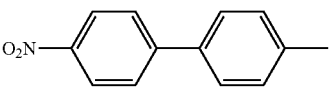 | N-{4-[5-(4'-Nitro-biphenyl-4-yl)-3-methyl-pyrazol-1-yl]-phenyl}-aminosulfonamide |
| 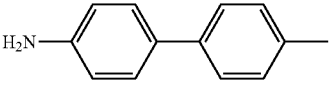 | N-{4-[5-(4'-Amino-biphenyl-4-yl)-3-methyl-pyrazol-1-yl]-phenyl}-aminosulfonamide |
| 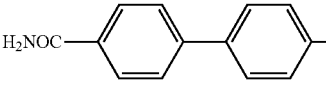 | 4'-[2-(4-Aminosulfonylamino-phenyl)-5-methyl-2H-pyrazol-3-yl]-biphenyl-4-carboxylic acid amide |
| 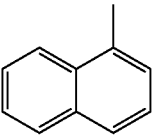 | N-[4-(5-Naphthalen-1-yl-3-methyl-pyrazol-1-yl)-phenyl]-aminosulfonamide |
| 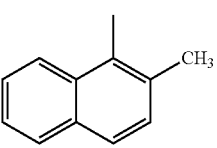 | N-{4-[5-(2-Methyl-naphthalen-1-yl)-3-methyl-pyrazol-1-yl]-phenyl}-aminosulfonamide |
| 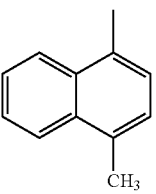 | N-{4-[5-(4-Methyl-naphthalen-1-yl)-3-methyl-pyrazol-1-yl]-phenyl}-aminosulfonamide |
| 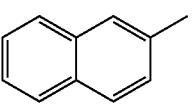 | N-[4-(5-Naphthalen-2-yl-3-methyl-pyrazol-1-yl)-phenyl]-aminosulfonamide |
| 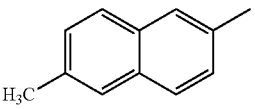 | N-{4-[5-(6-Methyl-naphthalen-2-yl)-3-methyl-pyrazol-1-yl]-phenyl}-aminosulfonamide |
| 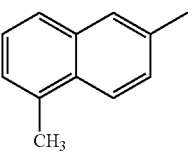 | N-{4-[5-(5-Methyl-naphthalen-2-yl)-3-methyl-pyrazol-1-yl]-phenyl}-aminosul |
| 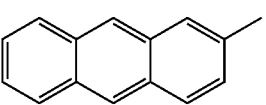 | N-[4-(5-Anthracen-2-yl-3-methyl-pyrazol-1-yl)-phenyl]-aminosulfonamide |
| 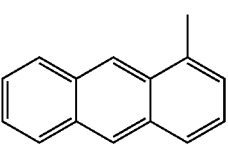 | N-[4-(5-Anthracen-1-yl-3-methyl-pyrazol-1-yl)-phenyl]-aminosulfonamide |

TABLE III-continued

Celecoxib Derivatives based on Formula IV

| Ar | Name |
|---|---|
| (9-methylanthracene structure) | N-[4-(5-Anthracen-9-yl-3-methyl-pyrazol-1-yl)-phenyl]-aminosulfonamide |
| (3-methylphenanthrene structure) | N-[4-(5-Phenanthren-3-yl-3-methyl-pyrazol-1-yl)-phenyl]-aminosulfonamide |
| (2-methylphenanthrene structure) | N-[4-(5-Phenanthren-2-yl-3-methyl-pyrazol-1-yl)-phenyl]-aminosulfonamide |
| (1-methylphenanthrene structure) | N-[4-(5-Phenanthren-1-yl-3-methyl-pyrazol-1-yl)-phenyl]-aminosulfonamide |
| (9-methyl-5,6-dihydrophenanthrene structure) | N-{4-[5-(5,6-Dihydro-phenanthren-9-yl)-3-methyl-pyrazol-1-yl]-phenyl}-aminosulfonamide |
| (4-methylphenanthrene structure) | N-[4-(5-Phenanthren-4-yl-3-methyl-pyrazol-1-yl)-phenyl]-aminosulfonamide |

Specific examples of compounds according to formula IV in which $R^1$ is trifluoromethyl are shown in Table IV, in $R^2$ is shown as the Ar group.

TABLE IV

Celecoxib Derivatives based on Formula IV

| Ar | Name |
|---|---|
| (phenyl) | N-[4-(5-Phenyl-3-trifluoromethyl-pyrazol-1-yl)-phenyl]-aminosulfonamide |
| H$_3$C—(phenyl)— | N-[4-(5-p-Tolyl-3-trifluoromethyl-pyrazol-1-yl)-phenyl]-sulfonamide (Wf10092301) |
| H$_3$CO—(phenyl)— | N-{4-[5-(4-Methoxy-phenyl)-3-trifluoromethyl-pyrazol-1-yl]-phenyl}-sulfonamide |

TABLE IV-continued

Celecoxib Derivatives based on Formula IV

| Ar | Name |
|---|---|
| F₃C—⟨phenyl⟩— | N-{4-[3-Trifluoromethyl-5-(4-trifluoromethyl-phenyl)-pyrazol-1-yl]-phenyl}-aminosulfonamide |
| Cl—⟨phenyl⟩— | N-{4-[5-(4-Chloro-phenyl)-3-trifluoromethyl-pyrazol-1-yl]-phenyl}-aminosulfonamide |
| F—⟨phenyl⟩— | N-{4-[5-(4-Fluoro-phenyl)-3-trifluoromethyl-pyrazol-1-yl]-phenyl}-aminosulfonamide |
| NC—⟨phenyl⟩— | N-{4-[5-(4-Cyano-phenyl)-3-trifluoromethyl-pyrazol-1-yl]-phenyl}-aminosulfonamide |
| O₂N—⟨phenyl⟩— | N-{4-[5-(4-Nitro-phenyl)-3-trifluoromethyl-pyrazol-1-yl]-phenyl}-aminosulfonamide |
| H₂N—⟨phenyl⟩— | N-{4-[5-(4--phenyl)-3-trifluoromethyl-pyrazol-1-yl]-phenyl}-aminosulfonamide |
| H₂NOC—⟨phenyl⟩— | 4-[2-(4-Aminosulfonyl-phenyl)-5-trifluoromethyl-2H-pyrazol-3-yl]-benzamide |
| 2,4-dimethylphenyl (H₃C, H₃C) | N-{4-[5-(3,4-Dimethyl-phenyl)-3-trifluoromethyl-pyrazol-1-yl]-phenyl}-aminosulfonamide |
| 3,4-dimethoxyphenyl (H₃CO, H₃CO) | N-{4-[5-(3,4-Dimethoxy-phenyl)-3-trifluoromethyl-pyrazol-1-yl]-phenyl}-aminosulfonamide |
| 3,4-dichlorophenyl (Cl, Cl) | N-{4-[5-(3,4-Dichloro-phenyl)-3-trifluoromethyl-pyrazol-1-yl]-phenyl}-aminosulfona |
| 3,4-difluorophenyl (F, F) | N-{4-[5-(3,4-Difluoro-phenyl)-3-trifluoromethyl-pyrazol-1-yl]-phenyl}-aminosulfona |
| biphenyl-4-yl | N-[4-(5-Biphenyl-4-yl-3-trifluoromethyl-pyrazol-1-yl)-phenyl]-aminosulfonamide (Wf10092201) |
| Cl—⟨phenyl⟩—⟨phenyl⟩— | N-{4-[5-(4'-Chloro-biphenyl-4-yl)-3-trifluoromethyl-pyrazol-1-yl]-phenyl}-aminosulfonamide |
| F—⟨phenyl⟩—⟨phenyl⟩— | N-{4-[5-(4'-Fluoro-biphenyl-4-yl)-3-trifluoromethyl-pyrazol-1-yl]-phenyl}-aminosulfonamide |

TABLE IV-continued

Celecoxib Derivatives based on Formula IV

| Ar | Name |
|---|---|
| 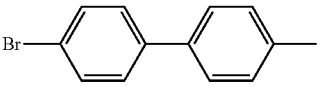 | N-{4-[5-(4'-Bromo-biphenyl-4-yl)-3-trifluoromethyl-pyrazol-1-yl]-phenyl}-aminosulfonamide (Wf10100401) |
| 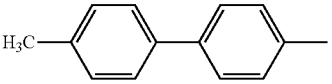 | N-{4-[5-(4'-Methyl-biphenyl-4-yl)-3-trifluoromethyl-pyrazol-1-yl]-phenyl}-aminosulfonamide (Wf10092001) |
| 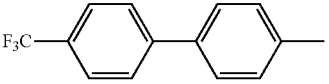 | N-{4-[5-(4'-Trifluoromethyl-biphenyl-4-yl)-3-trifluoromethyl-pyrazol-1-yl]-phenyl}-aminosulfonamide |
| 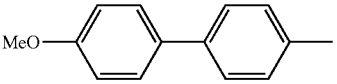 | N-{4-[5-(4'-Methoxy-biphenyl-4-yl)-3-trifluoromethyl-pyrazol-1-yl]-phenyl}-aminosulfonamide |
| 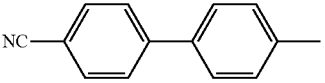 | N-{4-[5-(4'-Cyano-biphenyl-4-yl)-3-trifluoromethyl-pyrazol-1-yl]-phenyl}-aminosulfonamide |
| 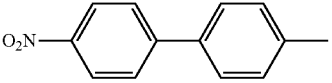 | N-{4-[5-(4'-Nitro-biphenyl-4-yl)-3-trifluoromethyl-pyrazol-1-yl]-phenyl}-aminosulfonamide |
| 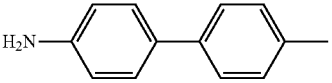 | N-{4-[5-(4'--biphenyl-4-yl)-3-trifluoromethyl-pyrazol-1-yl]-phenyl}-aminosulfonamide |
| 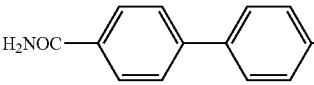 | 4'-[2-(4-Aminosulfonyl-phenyl)-5-trifluoromethyl-2H-pyrazol-3-yl]-biphenyl-4-carboxylic acid amide |
| 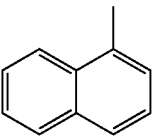 | N-[4-(5-Napthalen-1-yl-3-trifluoromethyl-pyrazol-1-yl)-phenyl]-aminosulfonamide |
| 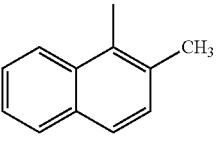 | N-{4-[5-(2-Methyl-naphthalen-1-yl)-3-trifluoromethyl-pyrazol-1-yl]-phenyl}-aminosulfonamide |
| 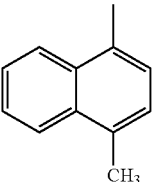 | N-{4-[5-(4-Methyl-naphthalen-1-yl)-3-trifluoromethyl-pyrazol-1-yl]-phenyl}-aminosulfonamide |
| 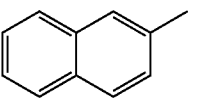 | N-[4-(5-Napthalen-2-yl-3-trifluoromethyl-pyrazol-1-yl)-phenyl]-aminosulfonamide (Wf10091801) |
| 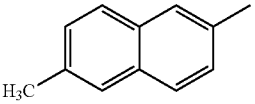 | N-{4-[5-(6-Methyl-naphthalen-2-yl)-3-trifluoromethyl-pyrazol-1-yl]-phenyl}-aminosulfonamide |

TABLE IV-continued

Celecoxib Derivatives based on Formula IV

| Ar | Name |
|---|---|
| (1-methyl-naphthalen-2-yl group, methyl at position shown with CH₃) | N-{4-[5-(5-Methyl-naphthalen-2-yl)-3-trifluoromethyl-pyrazol-1-yl]-phenyl}-aminosul |
| (anthracen-2-yl) | N-[4-(5-Anthracen-2-yl-3-trifluoromethyl-pyrazol-1-yl)-phenyl]-aminosulfonamide (Wf10100201) |
| (anthracen-1-yl) | N-[4-(5-Anthracen-1-yl-3-trifluoromethyl-pyrazol-1-yl)-phenyl]-aminosulfonamide |
| (anthracen-9-yl) | N-[4-(5-Anthracen-9-yl-3-trifluoromethyl-pyrazol-1-yl)-phenyl]-aminosulfonamide (Wf10091601) |
| (phenanthren-3-yl) | N-[4-(5-Phenanthren-3-yl-3-trifluoromethyl-pyrazol-1-yl)-phenyl]-aminosulfonamide |
| (phenanthren-2-yl) | N-[4-(5-Phenanthren-2-yl-3-trifluoromethyl-pyrazol-1-yl)-phenyl]-aminosulfonamide |
| (phenanthren-1-yl) | N-[4-(5-Phenanthren-1-yl-3-trifluoromethyl-pyrazol-1-yl)-phenyl]-aminosulfonamide |
| (5,6-dichloro-phenanthren-9-yl) | N-{4-[5-(5,6-Dichloro-phenanthren-9-yl)-3-trifluoromethyl-pyrazol-1-yl]-phenyl}-aminosulfonamide |
| (phenanthren-4-yl) | N-[4-(5-Phenanthren-4-yl-3-trifluoromethyl-pyrazol-1-yl)-phenyl]-aminosulfonamide |

Another aspect of the invention provides pyrazole compounds of formula V:

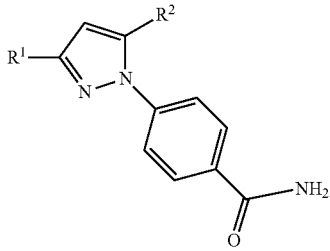

wherein $R^1$ is a methyl or trifluoromethyl moiety and $R^2$ is an aryl group selected from the group consisting of substituted and unsubstituted phenyl, biphenyl, naphthyl, anthracenyl, and phenanthrenyl groups.

In some embodiments, the compounds of formula V can include $R^2$ as an aryl group selected from the group consisting of

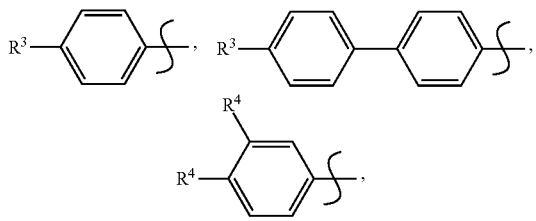

mono-methyl substituted naphthyl, and unsubstituted naphthyl, anthracenyl, and phananthracenyl groups, wherein $R^3$ is selected from the group consisting of hydrogen, chloro, fluoro, bromo, methyl, trifluoromethyl, methoxy, cyano, nitro, amino, and carboxamide moieties, and wherein $R^4$ is selected from the group consisting of methyl, methoxy, chloro, and fluoro moieties.

Separate embodiments of the compounds of formula V can include $R^1$ as either a methyl or trifluoromethyl substituent.

Specific examples of compounds according to formula V in which $R^1$ is methyl are shown in Table V, in which $R^2$ is shown as the Ar group.

TABLE V

Celecoxib Derivatives based on Formula V

| Ar | Name |
|---|---|
| phenyl | 4-(5-Phenyl-3-methyl-pyrazol-1-yl)-benzamide |
| H₃C–C₆H₄– | 4-(5-p-Tolyl-3-methyl-pyrazol-1-yl)-benzamide |
| H₃CO–C₆H₄– | 4-[5-(4-Methoxy-phenyl)-3-methyl-pyrazol-1-yl]-benzamide |
| F₃C–C₆H₄– | 4-[3-Methyl-5-(4-methyl-phenyl)-pyrazol-1-yl]-benzamide |
| Cl–C₆H₄– | 4-[5-(4-Chloro-phenyl)-3-methyl-pyrazol-1-yl]-benzamide |
| F–C₆H₄– | 4-[5-(4-Fluoro-phenyl)-3-methyl-pyrazol-1-yl]-benzamide |
| NC–C₆H₄– | 4-[5-(4-Cyano-phenyl)-3-methyl-pyrazol-1-yl]-benzamide |
| O₂N–C₆H₄– | 4-[5-(4-Nitro-phenyl)-3-methyl-pyrazol-1-yl]-benzamide |
| H₂N–C₆H₄– | 4-[5-(4-Amino-phenyl)-3-methyl-pyrazol-1-yl]-benzamide |

TABLE V-continued

Celecoxib Derivatives based on Formula V

| Ar | Name |
|---|---|
| 3,4-dimethylphenyl | 4-[5-(3,4-Dimethyl-phenyl)-3-methyl-pyrazol-1-yl]-benzamide |
| 3,4-dimethoxyphenyl | 4-[5-(3,4-Dimethoxy-phenyl)-3-methyl-pyrazol-1-yl]-benzamide |
| 3,4-dichlorophenyl | 4-[5-(3,4-Dichloro-phenyl)-3-methyl-pyrazol-1-yl]-benzamide |
| 3,4-difluorophenyl | 4-[5-(3,4-Difluoro-phenyl)-3-methyl-pyrazol-1-yl]-benzamide |
| biphenyl-4-yl | 4-(5-Biphenyl-4-yl-3-methyl-pyrazol-1-yl)-benzamide |
| 4'-chloro-biphenyl-4-yl | 4-[5-(4'-Chloro-biphenyl-4-yl)-3-methyl-pyrazol-1-yl]-benzamide |
| 4'-fluoro-biphenyl-4-yl | 4-[5-(4'-Fluoro-biphenyl-4-yl)-3-methyl-pyrazol-1-yl]-benzamide |
| 4'-bromo-biphenyl-4-yl | 4-[5-(4'-Bromo-biphenyl-4-yl)-3-methyl-pyrazol-1-yl]-benzamide |
| 4'-methyl-biphenyl-4-yl | 4-[5-(4'-Methyl-biphenyl-4-yl)-3-methyl-pyrazol-1-yl]-benzamide |
| 4'-trifluoromethyl-biphenyl-4-yl | 4-[5-(4'-Methyl-biphenyl-4-yl)-3-methyl-pyrazol-1-yl]-benzamide |
| 4'-methoxy-biphenyl-4-yl | 4-[5-(4'-Methoxy-biphenyl-4-yl)-3-methyl-pyrazol-1-yl]-benzamide |
| 4'-cyano-biphenyl-4-yl | 4-[5-(4'-Cyano-biphenyl-4-yl)-3-methyl-pyrazol-1-yl]-benzamide |
| 4'-nitro-biphenyl-4-yl | 4-[5-(4'-Nitro-biphenyl-4-yl)-3-methyl-pyrazol-1-yl]-benzamide |
| 4'-amino-biphenyl-4-yl | 4-[5-(4'-Amino-biphenyl-4-yl)-3-methyl-pyrazol-1-yl]-benzamide |

TABLE V-continued

Celecoxib Derivatives based on Formula V

| Ar | Name |
|---|---|
| | 4'-[2-(4-Carbamoyl-phenyl)-5-methyl-2H-pyrazol-3-yl]-biphenyl-4-carboxylic acid amide |
| | 4-(5-Naphthalen-1-yl-3-methyl-pyrazol-1-yl)-benzamide |
| | 4-[5-(2-Methyl-naphthalen-1-yl)-3-methyl-pyrazol-1-yl]-benzamide |
| | 4-[5-(4-Methyl-naphthalen-1-yl)-3-methyl-pyrazol-1-yl]-benzamide |
| | 4-(5-Naphthalen-2-yl-3-methyl-pyrazol-1-yl)-benzamide |
| | 4-[5-(6-Methyl-naphthalen-2-yl)-3-methyl-pyrazol-1-yl]-benzamide |
| | 4-[5-(5-Methyl-naphthalen-2-yl)-3-methyl-pyrazol-1-yl]-benzamide |
| | 4-(5-Anthracen-2-yl-3-methyl-pyrazol-1-yl)-benzamide |
| | 4-(5-Anthracen-1-yl-3-methyl-pyrazol-1-yl)-benzamide |
| | 4-(5-Anthracen-9-yl-3-methyl-pyrazol-1-yl)-benzamide |

TABLE V-continued

Celecoxib Derivatives based on Formula V

| Ar | Name |
|---|---|
|  | 4-(5-Phenanthren-3-yl-3-methyl-pyrazol-1-yl)-benzamide |
|  | 4-(5-Phenanthren-2-yl-3-methyl-pyrazol-1-yl)-benzamide |
|  | 4-(5-Phenanthren-1-yl-3-methyl-pyrazol-1-yl)-benzamide |
|  | 4-(5-Phenanthren-9-yl-3-methyl-pyrazol-1-yl)-benzamide |
|  | 4-(5-Phenanthren-4-yl-3-methyl-pyrazol-1-yl)-benzamide |

Specific examples of compounds according to formula V in which $R^1$ is trifluoromethyl are shown in Table VI, in which $R^2$ is shown as the Ar group.

TABLE VI

Celecoxib Derivatives based on Formula V

| Ar | Name |
|---|---|
|  | 4-(5-Phenyl-3-trifluoromethyl-pyrazol-1-yl)-benzamide |
| H₃C— | 4-(5-p-Tolyl-3-trifluoromethyl-pyrazol-1-yl)-benzamide |
| H₃CO— | 4-[5-(4-Methoxy-phenyl)-3-trifluoromethyl-pyrazol-1-yl]-benzamide |
| F₃C— | 4-[3-Trifluoromethyl-5-(4-trifluoromethyl-phenyl)-pyrazol-1-yl]-benzamide |
| Cl— | 4-[5-(4-Chloro-phenyl)-3-trifluoromethyl-pyrazol-1-yl]-benzamide |

TABLE VI-continued

Celecoxib Derivatives based on Formula V

| Ar | Name |
|---|---|
| 4-F-phenyl | 4-[5-(4-Fluoro-phenyl)-3-trifluoromethyl-pyrazol-1-yl]-benzamide |
| 4-NC-phenyl | 4-[5-(4-Cyano-phenyl)-3-trifluoromethyl-pyrazol-1-yl]-benzamide |
| 4-O$_2$N-phenyl | 4-[5-(4-Nitro-phenyl)-3-trifluoromethyl-pyrazol-1-yl]-benzamide |
| 4-H$_2$N-phenyl | 4-[5-(4-Amino-phenyl)-3-trifluoromethyl-pyrazol-1-yl]-benzamide |
| 3,4-dimethyl-phenyl | 4-[5-(3,4-Dimethyl-phenyl)-3-trifluoromethyl-pyrazol-1-yl]-benzamide |
| 3,4-dimethoxy-phenyl | 4-[5-(3,4-Dimethoxy-phenyl)-3-trifluoromethyl-pyrazol-1-yl]-benzamide |
| 3,4-dichloro-phenyl | 4-[5-(3,4-Dichloro-phenyl)-3-trifluoromethyl-pyrazol-1-yl]-benzamide |
| 3,4-difluoro-phenyl | 4-[5-(3,4-Difluoro-phenyl)-3-trifluoromethyl-pyrazol-1-yl]-benzamide |
| biphenyl-4-yl | 4-[5-Biphenyl-4-yl-3-trifluoromethyl-pyrazol-1-yl)-benzamide |
| 4'-Cl-biphenyl-4-yl | 4-[5-(4'-Chloro-biphenyl-4-yl)-3-trifluoromethyl-pyrazol-1-yl]-benzamide |
| 4'-F-biphenyl-4-yl | 4-[5-(4'-Fluoro-biphenyl-4-yl)-3-trifluoromethyl-pyrazol-1-yl]-benzamide |
| 4'-Br-biphenyl-4-yl | 4-[5-(4'-Bromo-biphenyl-4-yl)-3-trifluoromethyl-pyrazol-1-yl]-benzamide |
| 4'-H$_3$C-biphenyl-4-yl | 4-[5-(4'-Methyl-biphenyl-4-yl)-3-trifluoromethyl-pyrazol-1-yl]-benzamide |
| 4'-F$_3$C-biphenyl-4-yl | 4-[5-(4'-Trifluoromethyl-biphenyl-4-yl)-3-trifluoromethyl-pyrazol-1-yl]-benzamide |

TABLE VI-continued

Celecoxib Derivatives based on Formula V

| Ar | Name |
|---|---|
| 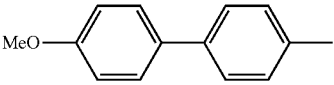 | 4-[5-(4'-Methoxy-biphenyl-4-yl)-3-trifluoromethyl-pyrazol-1-yl]-benzamide |
| 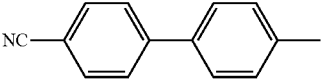 | 4-[5-(4'-Cyano-biphenyl-4-yl)-3-trifluoromethyl-pyrazol-1-yl]-benzamide |
| 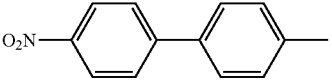 | 4-[5-(4'-Nitro-biphenyl-4-yl)-3-trifluoromethyl-pyrazol-1-yl]-benzamide |
| 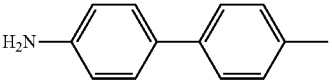 | 4-[5-(4'-Amino-biphenyl-4-yl)-3-trifluoromethyl-pyrazol-1-yl]-benzamide |
| 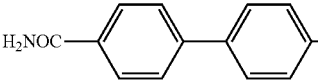 | 4'-[2-(4-Carbamoyl-phenyl)-5-trifluoromethyl-2H-pyrazol-3-yl]-biphenyl-4-carboxylic acid amide |
| 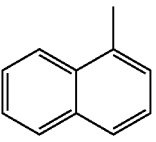 | 4-(5-Naphthalen-1-yl-3-trifluoromethyl-pyrazol-1-yl)-benzamide |
| 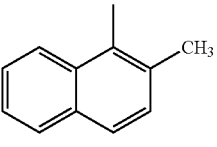 | 4-[5-(2-Methyl-naphthalen-1-yl)-3-trifluoromethyl-pyrazol-1-yl]-benzamide |
| 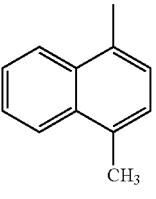 | 4-[5-(4-Methyl-naphthalen-1-yl)-3-trifluoromethyl-pyrazol-1-yl]-benzamide de |
| 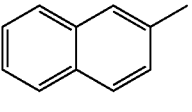 | 4-(5-Naphthalen-2-yl-3-trifluoromethyl-pyrazol-1-yl)-benzamide |
| 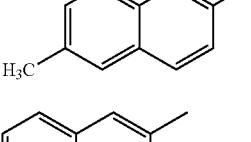 | 4-[5-(6-Methyl-naphthalen-2-yl)-3-trifluoromethyl-pyrazol-1-yl]-benzamide |
| 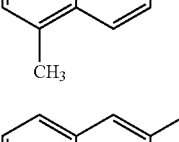 | 4-[5-(5-Methyl-naphthalen-2-yl)-3-trifluoromethyl-pyrazol-1-yl]-benzamide |
| 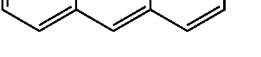 | 4-(5-Anthracen-2-yl-3-trifluoromethyl-pyrazol-1-yl)-benzamide |

TABLE VI-continued

Celecoxib Derivatives based on Formula V

| Ar | Name |
|---|---|
| | 4-(5-Anthracen-1-yl-3-trifluoromethyl-pyrazol-yl)-benzamide |
| | 4-(5-Anthracen-9-yl-3-trifluoromethyl-pyrazol-1-yl)-benzamide |
| | 4-(5-Phenanthren-3-yl-3-trifluoromethyl-pyrazol-1-yl)-benzamide |
| | 4-(5-Phenanthren-2-yl-3-trifluoromethyl-pyrazol-1-yl)-benzamide |
| | 4-(5-Phenanthren-1-yl-3-trifluoromethyl-pyrazol-1-yl)-benzamide |
| | 4-(5-Phenanthren-9-yl-3-trifluoromethyl-pyrazol-1-yl)-benzamide |
| | 4-(5-Phenanthren-4-yl-3-trifluoromethyl-pyrazol-1-yl)-benzamide |

Another aspect of the invention provides pyrazole compounds of formula VI:

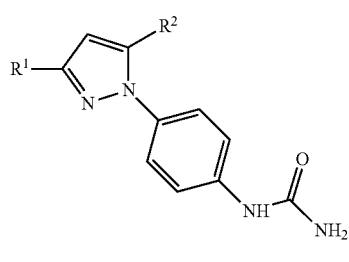

VI wherein $R^1$ is a methyl or trifluoromethyl moiety and $R^2$ is an aryl group selected from the group consisting of substituted and substituted phenyl, biphenyl, naphthyl, anthracenyl, and phenanthrenyl groups.

In some embodiments, the compounds of formula VI can include $R^2$ as an aryl group selected from the group consisting of -continued

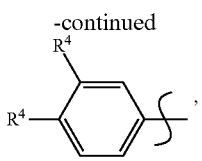

mono-methyl substituted naphthyl, and unsubstituted naphthyl, anthracenyl, and phenanthrenyl groups, wherein $R^3$ is selected from the group consisting of hydrogen, chloro, fluoro, bromo, methyl, trifluoromethyl, methoxy, cyano, nitro, amino, and carboxamide moieties, and wherein $R^4$ is selected from the group consisting of methyl, methoxy, chloro, and fluoro moieties.

Separate embodiments of the compounds of formula VI can include $R^1$ as either a methyl or trifluoromethyl substituent.

Specific examples of compounds according to formula VI in which $R^1$ is methyl are shown in Table VII, in which $R^2$ is shown as the Ar group.

TABLE VII

Celecoxib Derivatives based on Formula VI

| Ar | Name |
|---|---|
|  | [4-(3-Methyl-5-phenyl-pyrazol-1-yl)-phenyl]-urea |
|  | {4-[5-(4-Methyl-phenyl)-3-methyl-pyrazol-1-yl]-phenyl}-urea |
|  | {4-[5-(4-Methoxy-phenyl)-3-methyl-pyrazol-1-yl]-phenyl}-urea |
|  | {4-[5-(4-Trifluoromethyl-phenyl)-3-methyl-pyrazol-1-yl]-phenyl}-urea |
|  | {4-[5-(4-Chloro-phenyl)-3-methyl-pyrazol-1-yl]-phenyl}-urea |
|  | {4-[5-(4-Fluoro-phenyl)-3-methyl-pyrazol-1-yl]-phenyl}-urea |
|  | {4-[5-(4-Cyano-phenyl)-3-methyl-pyrazol-1-yl]-phenyl}-urea |
|  | {4-[5-(4-Nitro-phenyl)-3-methyl-pyrazol-1-yl]-phenyl}-urea |
|  | {4-[5-(4-Amino-phenyl)-3-methyl-pyrazol-1-yl]-phenyl}-urea |
|  | 4-[5-Methyl-2-(4-ureido-phenyl)-2H-pyrazol-3-yl]-benzamide |
|  | {4-[5-(3,4-Dimethyl-phenyl)-3-methyl-pyrazol-1-yl]-phenyl}-urea |
|  | {4-[5-(3,4-Dimethoxy-phenyl)-3-methyl-pyrazol-1-yl]-phenyl}-urea |

TABLE VII-continued

Celecoxib Derivatives based on Formula VI

| Ar | Name |
|---|---|
| 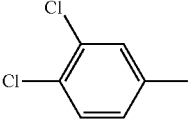 | {4-[5-(3,4-Dichloro-phenyl)-3-methyl-pyrazol-1-yl]-phenyl}-urea |
| 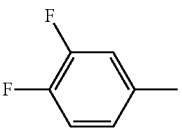 | {4-[5-(3,4-Difluoro-phenyl)-3-methyl-pyrazol-1-yl]-phenyl}-urea |
| 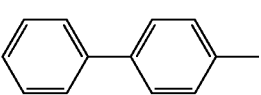 | [4-(5-Biphenyl-4-yl-3-methyl-pyrazol-1-yl)-phenyl]-urea |
| 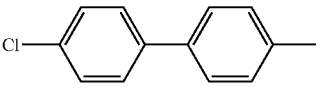 | {4-[5-(4'-Chloro-biphenyl-4-yl)-3-methyl-pyrazol-1-yl]-phenyl}-urea |
| 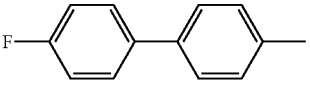 | {4-[5-(4'-Fluoro-biphenyl-4-yl)-3-methyl-pyrazol-1-yl]-phenyl}-urea |
| 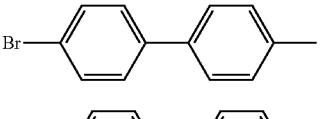 | {4-[5-(4'-Bromo-biphenyl-4-yl)-3-methyl-pyrazol-1-yl]-phenyl}-urea |
| 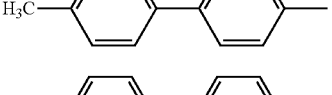 | {4-[5-(4'-Methyl-biphenyl-4-yl)-3-methyl-pyrazol-1-yl]-phenyl}-urea |
| 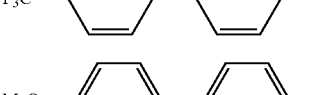 | {4-[5-(4'-Trifluoromethyl-biphenyl-4-yl)-3-methyl-pyrazol-1-yl]-phenyl}-urea |
| 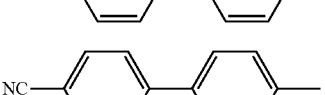 | {4-[5-(4'-Methoxy-biphenyl-4-yl)-3-methyl-pyrazol-1-yl]-phenyl}-urea |
| 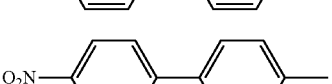 | {4-[5-(4'-Cyano-biphenyl-4-yl)-3-methyl-pyrazol-1-yl]-phenyl}-urea |
| 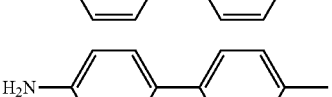 | {4-[5-(4'-Nitro-biphenyl-4-yl)-3-methyl-pyrazol-1-yl]-phenyl}-urea |
| 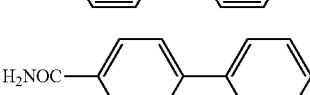 | {4-[5-(4'-Amino-biphenyl-4-yl)-3-methyl-pyrazol-1-yl]-phenyl}-urea |
| 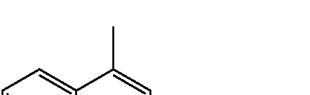 | 4'-[5-Methyl-2-(4-ureido-phenyl)-2H-pyrazol-3-yl]-biphenyl-4-carboxylic acid amide |
| 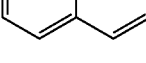 | [4-(3-Methyl-5-naphthalen-1-yl-pyrazol-1-yl)-phenyl]-urea |

TABLE VII-continued

Celecoxib Derivatives based on Formula VI

| Ar | Name |
|---|---|
| 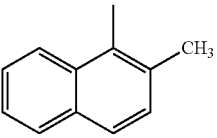 | {4-[3-Methyl-5-(3-methyl-naphthalen-1-yl)-pyrazol-1-yl]-phenyl}-urea |
| 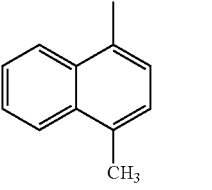 | {4-[3-Methyl-5-(4-methyl-naphthalen-1-yl)-pyrazol-1-yl]-phenyl}-urea |
| 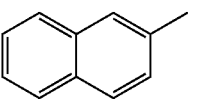 | [4-(3-Methyl-5-naphthalen-2-yl-pyrazol-1-yl)-phenyl]-urea |
| 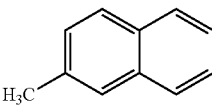 | {4-[3-Methyl-5-(6-methyl-naphthalen-2-yl)-pyrazol-1-yl]-phenyl}-urea |
| 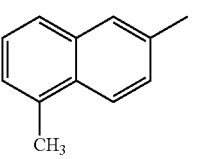 | {4-[3-Methyl-5-(5-methyl-naphthalen-2-yl)-pyrazol-1-yl]-phenyl}-urea |
| 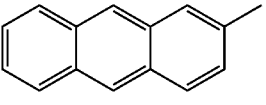 | [4-(5-Anthracen-2-yl-3-methyl-pyrazol-1-yl)-phenyl]-urea |
| 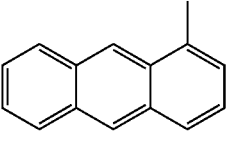 | [4-(5-Anthracen-1-yl-3-methyl-pyrazol-1-yl)-phenyl]-urea |
| 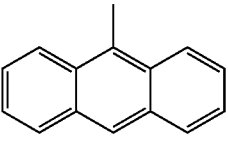 | [4-(5-Anthracen-1-yl-9-methyl-pyrazol-1-yl)-phenyl]-urea |
| 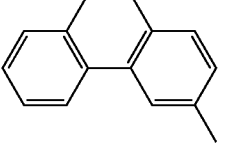 | [4-(3-Methyl-5-phenanthren-3-yl-pyrazol-1-yl)-phenyl]-urea |
| 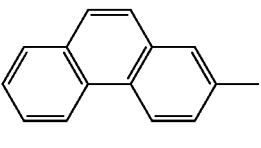 | [4-(3-Methyl-5-phenanthren-2-yl-pyrazol-1-yl)-phenyl]-urea |

TABLE VII-continued

Celecoxib Derivatives based on Formula VI

| Ar | Name |
|---|---|
| (3-methyl-phenanthren-1-yl structure) | [4-(3-Methyl-5-phenanthren-1-yl-pyrazol-1-yl)-phenyl]-urea |
| (3-methyl-phenanthren-9-yl structure) | [4-(3-Methyl-5-phenanthren-9-yl-pyrazol-1-yl)-phenyl]-urea |
| (3-methyl-phenanthren-4-yl structure) | [4-(3-Methyl-5-phenanthren-4-yl-pyrazol-1-yl)-phenyl]-urea |

Specific examples of compounds according to formula VI in which $R^1$ is trifluormethyl are shown in Table VIII, in which $R^2$ is shown as the Ar group.

TABLE VIII

Celecoxib Derivatives based on Formula VI

| Ar | Name |
|---|---|
| phenyl | [4-(5-Phenyl-3-trifluoromethyl-pyrazol-1-yl)-phenyl]-urea |
| H₃C—phenyl | [4-(5-p-Tolyl-3-trifluoromethyl-pyrazol-1-yl)-phenyl]-urea |
| H₃CO—phenyl | {4-[5-(4-Methoxy-phenyl)-3-trifluoromethyl-pyrazol-1-yl]-phenyl}-urea |
| F₃C—phenyl | {4-[3-Trifluoromethyl-5-(4-trifluoromethyl-phenyl)-pyrazol-1-yl]-phenyl}-urea |
| Cl—phenyl | {4-[5-(4-Chloro-phenyl)-3-trifluoromethyl-pyrazol-1-yl]-phenyl}-urea |
| F—phenyl | {4-[5-(4-Fluoro-phenyl)-3-trifluoromethyl-pyrazol-1-yl]-phenyl}-urea |
| NC—phenyl | {4-[5-(4-Cyano-phenyl)-3-trifluoromethyl-pyrazol-1-yl]-phenyl}-urea |
| O₂N—phenyl | {4-[5-(4-Nitro-phenyl)-3-trifluoromethyl-pyrazol-1-yl]-phenyl}-urea |

TABLE VIII-continued

Celecoxib Derivatives based on Formula VI

| Ar | Name |
|---|---|
| H₂N–C₆H₄– | {4-[5-(4-Amino-phenyl)-3-trifluoromethyl-pyrazol-1-yl]-phenyl}-urea |
| H₂NOC–C₆H₄– | 4-[5-Trifluoromethyl-2-(4-ureido-phenyl)-2H-pyrazol-3-yl]-benzamide |
| 3,4-(H₃C)₂–C₆H₃– | {4-[5-(3,4-Ditrifluoromethyl-phenyl)-3-trifluoromethyl-pyrazol-1-yl]-phenyl}-urea |
| 3,4-(H₃CO)₂–C₆H₃– | {4-[5-(3,4-Dimethoxy-phenyl)-3-trifluoromethyl-pyrazol-1-yl)-phenyl}-urea |
| 3,4-Cl₂–C₆H₃– | {4-[5-(3,4-Dichloro-phenyl)-3-trifluoromethyl-pyrazol-1-yl]-phenyl}-urea |
| 3,4-F₂–C₆H₃– | {4-[5-(3,4-Difluoro-phenyl)-3-trifluoromethyl-pyrazol-1-yl]-phenyl}-urea |
| biphenyl | [4-(5-Biphenyl-4-yl-3-trifluoromethyl-pyrazol-1-yl)-phenyl]-urea |
| Cl–C₆H₄–C₆H₄– | {4-[5-(4'-Chloro-biphenyl-4-yl)-3-trifluoromethyl-pyrazol-1-yl]-phenyl}-urea |
| F–C₆H₄–C₆H₄– | {4-[5-(4'-Fluoro-biphenyl-4-yl)-3-trifluoromethyl-pyrazol-1-yl]-phenyl}-urea |
| Br–C₆H₄–C₆H₄– | {4-{5-(4'-Bromo-biphenyl-4-yl)-3-trifluoromethyl-pyrazol-1-yl]-phenyl}-urea |
| H₃C–C₆H₄–C₆H₄– | {4-[5-(4'-Trifluoromethyl-biphenyl-4-yl)-3-trifluoromethyl-pyrazol-1-yl]-phenyl}-urea |
| F₃C–C₆H₄–C₆H₄– | {4-[5-(4'-Trifluorotrifluoromethyl-biphenyl-4-yl)-3-trifluoromethyl-pyrazol-1-yl]-phenyl)-urea |
| MeO–C₆H₄–C₆H₄– | {4-[5-(4'-Methoxy-biphenyl-4-yl)-3-trifluoromethyl-pyrazol-1-yl]-phenyl}-urea |
| NC–C₆H₄–C₆H₄– | {4-[5-(4'-Cyano-biphenyl-4-yl)-3-trifluoromethyl-pyrazol-1-yl]-phenyl}-urea |

TABLE VIII-continued

Celecoxib Derivatives based on Formula VI

| Ar | Name |
|---|---|
| 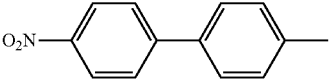 | {4-[5-(4'-Nitro-biphenyl-4-yl)-3-trifluoromethyl-pyrazol-1-yl]-phenyl}-urea |
| 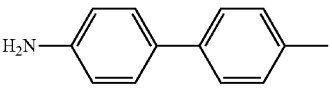 | {4-[5-(4'-Amino-biphenyl-4-yl)-3-trifluoromethyl-pyrazol-1-yl]-phenyl]-urea |
| 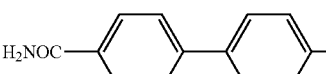 | 4'-[5-Trifluoromethyl-2-(4-ureido-phenyl)-2H-pyrazol-3-yl]-biphenyl-4-carboxylic acid amide |
| 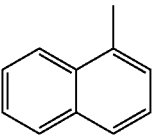 | [4-(3-Trifluoromethyl-5-naphthalen-1-yl-pyrazol-1-yl)-phenyl}-urea |
| 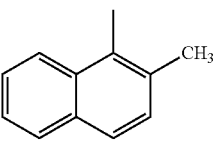 | {4-[3-Trifluoromethyl-5-(3-trifluoromethyl-naphthalen-1-yl)-pyrazol-1-yl]-phenyl}-urea |
| 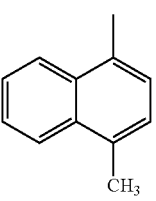 | {4-[3-Trifluoromethyl-5-(4-trifluoromethyl-naphthalen-1-yl)-pyrazol-1-yl]-phenyl}-urea |
| 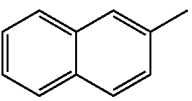 | [4-(3-Trifluoromethyl-5-naphthalen-2-yl-pyrazol-1-yl)-phenyl]-urea |
| 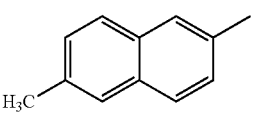 | {4-[3-Trifluoromethyl-5-(6-trifluoromethyl-naphthalen-2-yl)-pyrazol-1-yl]-phenyl}-urea |
| 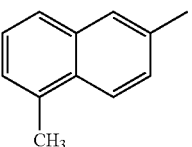 | {4-[3-Trifluoromethyl-5-(5-trifluoromethyl-naphthalen-2-yl)-pyrazol-1-yl]-phenyl}-urea |
| 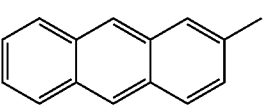 | [4-(5-Anthracen-2-yl-3-trifluoromethyl-pyrazol-1-yl)-phenyl]-urea |
| 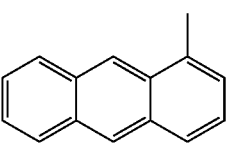 | [4-(5-Anthracen-1-yl-3-trifluoromethyl-pyrazol-1-yl)-phenyl]-urea |

TABLE VIII-continued

Celecoxib Derivatives based on Formula VI

| Ar | Name |
|---|---|
| | [4-(5-Anthracen-1-yl-9-trifluoromethyl-pyrazol-1-yl)-phenyl]-urea |
| | [4-(3-Trifluoromethyl-5-phenanthren-3-yl-pyrazol-1-yl)-phenyl]-urea |
| | [4-(3-Trifluoromethyl-5-phenanthren-2-yl-pyrazol-1-yl)-phenyl]-urea |
| | [4-(3-Trifluoromethyl-5-phenanthren-1-yl-pyrazol-1-yl)-phenyl]-urea |
| | [4-(3-Trifluoromethyl-5-phenanthren-9-yl-pyrazol-1-yl)-phenyl]-urea |
| | [4-(3-Trifluoromethyl-5-phenanthren-4-yl-pyrazol-1-yl)-phenyl]-urea |

Treatment of *Staphylococcus* Using Celecoxib Derivatives

The present invention provides methods for treating or preventing infection by *Staphylococcus* in a subject using celecoxib derivatives. *Staphylococcus* is a genus of Gram-positive bacteria that includes a number of pathogenic species such as *Staphylococcus aureus* and *Staphylococcus epidermidis*. *Staphylococcus* bacteria can cause a wide variety of infections in subjects through either toxin production or invasion. *Staphylococcus aureus* (formerly also known as *Staphylococcus pyogenes*) is a species of *Staphylococcus* that is able to survive on dry surfaces such as skin, and is the most common cause of Staph infections. *S. aureus* can cause a range of illnesses from minor skin infections to life-threatening diseases such as pneumonia, meningitis, osteomyelitis, endocarditis, toxic shock syndrome (TSS), and sepsis. It is one of the most common causes of hospital (i.e. nosocomial) infections, typically causing postsurgical wound infections.

In addition to providing a method for treating or preventing infection by *Staphylococcus aureus*, the celecoxib derivatives of the present invention are also useful for treating methicillin-resistant *Staphylococcus aureus*, which may also be called multidrug-resistant *Staphylococcus aureus* or oxacillin-resistant *Staphylococcus aureus* (ORSA). MRSA has developed resistance to beta-lactam antibiotics which include the penicillins (methicillin, dicloxacillin, nafcillin, oxacillin, etc.) and the cephalosporins.

Celecoxib derivatives of the invention can be used for treatment by administered a therapeutically effective amount of the celecoxib derivative in a pharmaceutical carrier to a subject that is already infected by *Staphylococcus*. In one embodiment of therapeutic administration, administration of the celecoxib derivatives are effective to eliminate the infection; in another embodiment, administration of the celecoxib derivatives is effective to decrease the severity of the infection. The subject is preferably a mammal, such as a domesticated farm animal (e.g., cow, horse, pig) or pet (e.g., dog, cat). More preferably, the subject is a human. Alternately or in addition, celecoxib derivatives of the invention can be administered prophylactically to a subject prior to exposure to infection by *Staphylococcus*. Prophylactic administration, also referred to as prevention, is effective to decrease the likelihood of the subsequent infection in the mammal, or decrease the severity of *Staphylococcus* infection that subsequently occurs.

Administration and Formulation of Celecoxib Derivatives

The present invention also provides pharmaceutical compositions that include celecoxib derivatives such as those defined by formula I as an active ingredient, and a pharmaceutically acceptable liquid or solid carrier or carriers, in combination with the active ingredient. Any of the compounds described above as being suitable for the treatment of *Staphylococcus* can be included in pharmaceutical compositions of the invention.

The celecoxib derivatives can be administered as pharmaceutically acceptable salts. Pharmaceutically acceptable salt refers to the relatively non-toxic, inorganic and organic acid addition salts of the celecoxib derivatives. These salts can be prepared in situ during the final isolation and purification of the celecoxib derivative, or by separately reacting a purified celecoxib derivative with a suitable counterion, depending on the nature of the celecoxib derivative, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more celecoxib derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The celecoxib derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the celecoxib derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of celecoxib derivative (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, N.Y., (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed.

Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

General Procedures for the Preparation of Celecoxib Derivatives

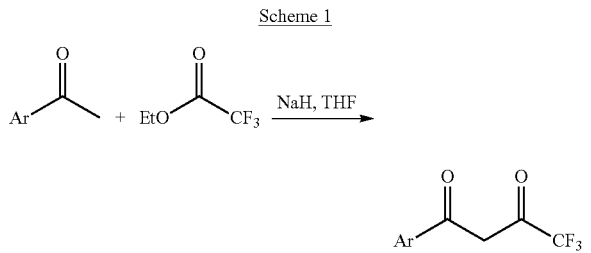

Scheme 1

As shown in Scheme 1, the ketone (10 mmol) was added slowly to a mixture of NaH (10 mmol) and ethyl trifluoroacetate (11 mmol) in THF. The resulting reaction mixture was stirred at room temperature overnight, concentrated and the residue was dissolved into water. The reaction mixtures was then extracted with ethyl acetate 3× and the combined organic layers were washed with brine and dried with sodium sulfate. The product was purified with column chromatograph (silica gel) afford diketone product.

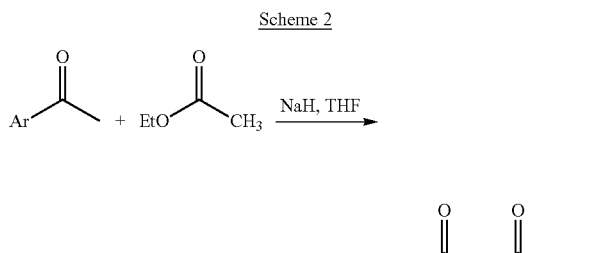

Scheme 2

To a mixture of NaOEt (10 mmol) and ethyl acetate (12.5 mmol) in THF, the ketone (10 mmol) was added slowly, as shown in Scheme 2. The resulting reaction mixture was stirred at room temperature overnight, concentrated and the residue was dissolved into water. The reaction mixture was then extracted with ethyl acetate 3× and the combined organic layers were washed with brine and dried with sodium sulfate. The product was purified with column chromatograph (silica gel) afford diketone product.

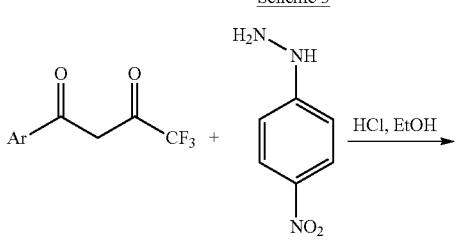

Scheme 3

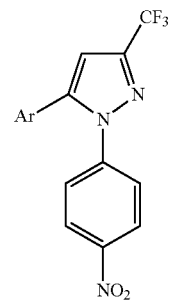

As shown in Scheme 3, the reaction mixture of diketone (6 mmol), 4-nitrophenyl hydrazine (6.6 mmol), and conc. HCl (2 eq) in ethyl alcohol was heated to reflux for 5 hrs. The resulting reaction mixture was concentrated and purified with column chromatography (silica gel), giving the pure pyrazole ring product.

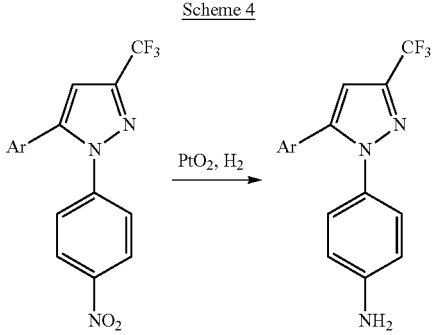

Scheme 4

The reaction mixture of nitro compound (3 mmol), platinum oxide (PtO$_2$, 0.1 mmol) in ethyl alcohol was stirred overnight under H$_2$ atmosphere as shown in Scheme 4. The resulting reaction mixture was filtered and washed with ethyl acetate. The combined filtrate was concentrated and the residue was purified with column chromatography (silica gel) to give the amine product.

Scheme 5

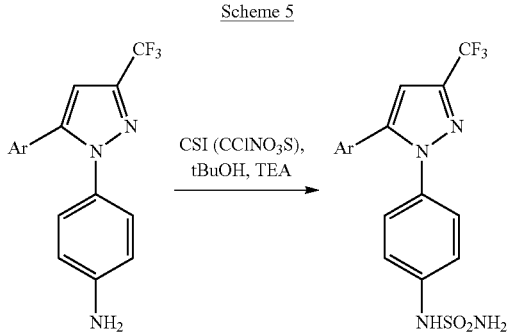

CSI (1 eq.) was added dropwise to a ice-cold solution of tert-butanol (1 mmol) in anhydrous methylene chloride, as shown in Scheme 5. The resulting reaction solution was added to a mixture of amine (1 mmol) and TEA (1.5 mmol) in methylene chloride. The final reaction mixture was stirred at room temperature for 1 hr., concentrated and re-dissolved in methylene chloride and treated with TFA. The reaction mixture was then washed with 10% sodium bicarbonate solution, dried with sodium sulfate and concentrated, and purified with column chromatograph (silica gel) afford pure product.

Scheme 6

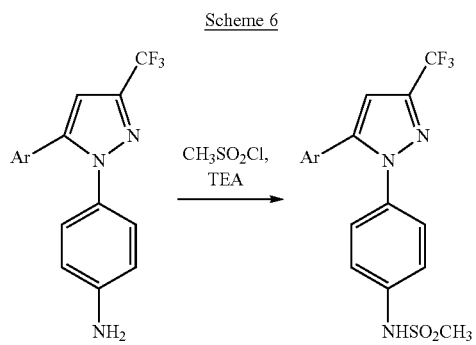

Methanesulfonyl chloride (1 mmol) was added to a cooled solution of aniline (1 mmol) and TEA (2.5 mmol) in methylene chloride. The resulting solution was stirred 0° C. for 1 hr. water was added and the mixture was extracted with methylene chloride. The combined organic layers were dried, filtered, and concentrated. The residue was purified with column chromatography (silica gel), affording the pure product.

Scheme 7

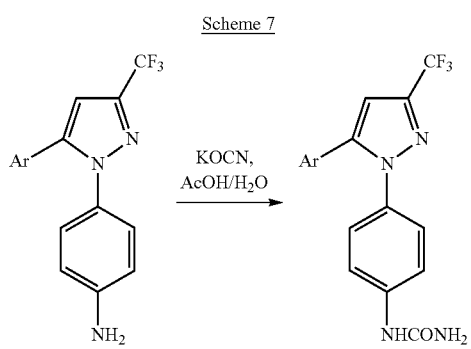

Potassium cyanate (1 mmol), dissolved in 10% acetic acid, was added to an equimolar amount of aniline, kept in water as a concentrated solution or suspension, at room temperature as shown in Scheme 7. A gas was formed ($CO_2$ in a side reaction) and the urea precipitated as a solid. It was recrystallized from water.

Scheme 8

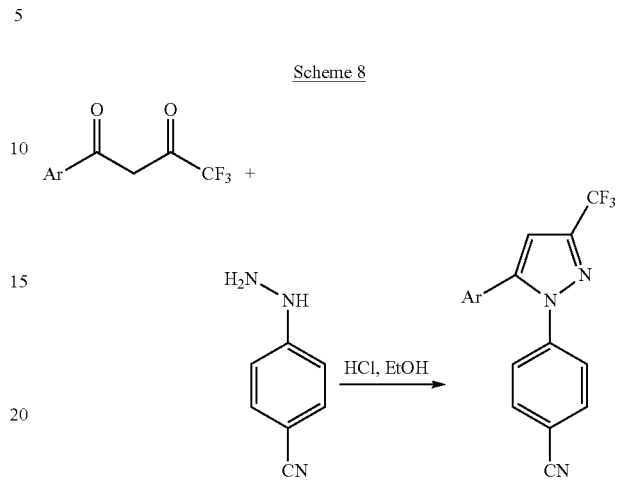

The reaction mixture of diketone (1 mmol), 4-nitrophenyl hydrazine (1.1 mmol), and conc. HCl (2 eq) in ethyl alcohol was heated to reflux for 5 hrs as shown in Scheme 8. The resulting reaction mixture was concentrated and purified with column chromatography (silica gel) to give the pure pyrazole ring product.

Scheme 9

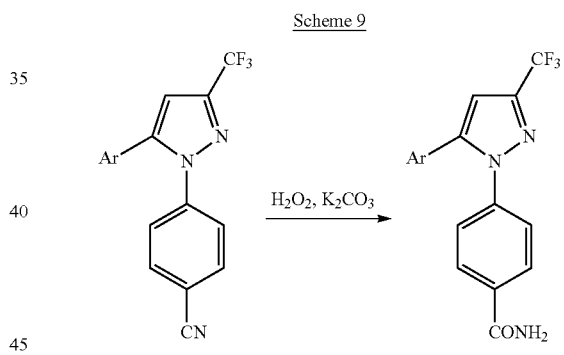

To a solution of the nitrile (0.5 mmol) in DMSO (1 mL) cooled in an ice-water bath, sodium carbonate (1 mmol) and hydrogen peroxide (30%, 0.2 mL) were added and the resulting reaction mixture was stirred at 20° C. for 3 hrs, after which water (3 mL) was added. See Scheme 9. The white solid was precipitated, filtered, and washed with water, affording the final product.

Example 2

Identification of Novel Anti-*Staphylococcus* Agents

Previously, the inventors obtained evidence that the cyclooxygenase-2 (COX-2) inhibitor celecoxib and its derivatives exhibited unique antimicrobial activities against various pathogenic bacteria in vitro. Chiu et al., Antimicrob Agents Chemother 53, 5236-44 (2009); Chiu et al., J Biomed Sci 16, 110 (2009); Chiu et al., Antimicrob Agents Chemother 53, 2998-3002 (2009).

As described herein, the inventors have demonstrated that celecoxib directly suppresses the growth of *S. aureus, S.* epidermidis and MRSA, while the more potent COX-2 inhibitor rofecoxib was ineffective. As celecoxib has been shown to suppress cancer cell proliferation, in part, by competing ATP binding of certain signaling kinases, such as phosphoinositide-dependent kinase-1 (PDK-1) and cyclin-dependent kinases (CDKs), and endoplasmic reticulum Ca2+-ATPases, the inventors hypothesized that celecoxib mediates the bacterial killing by blocking ATP-dependent enzymes or transporters that are crucial to cell survival. See Kulp et al., Cancer Res., 64, 1444-1451 (2004); Lin et al., Mol. Cancer Ther., 3, 1671-1680 (2004); Johnson et al., Biochem. J., 366, 831-7 (2002).

Figure 2:
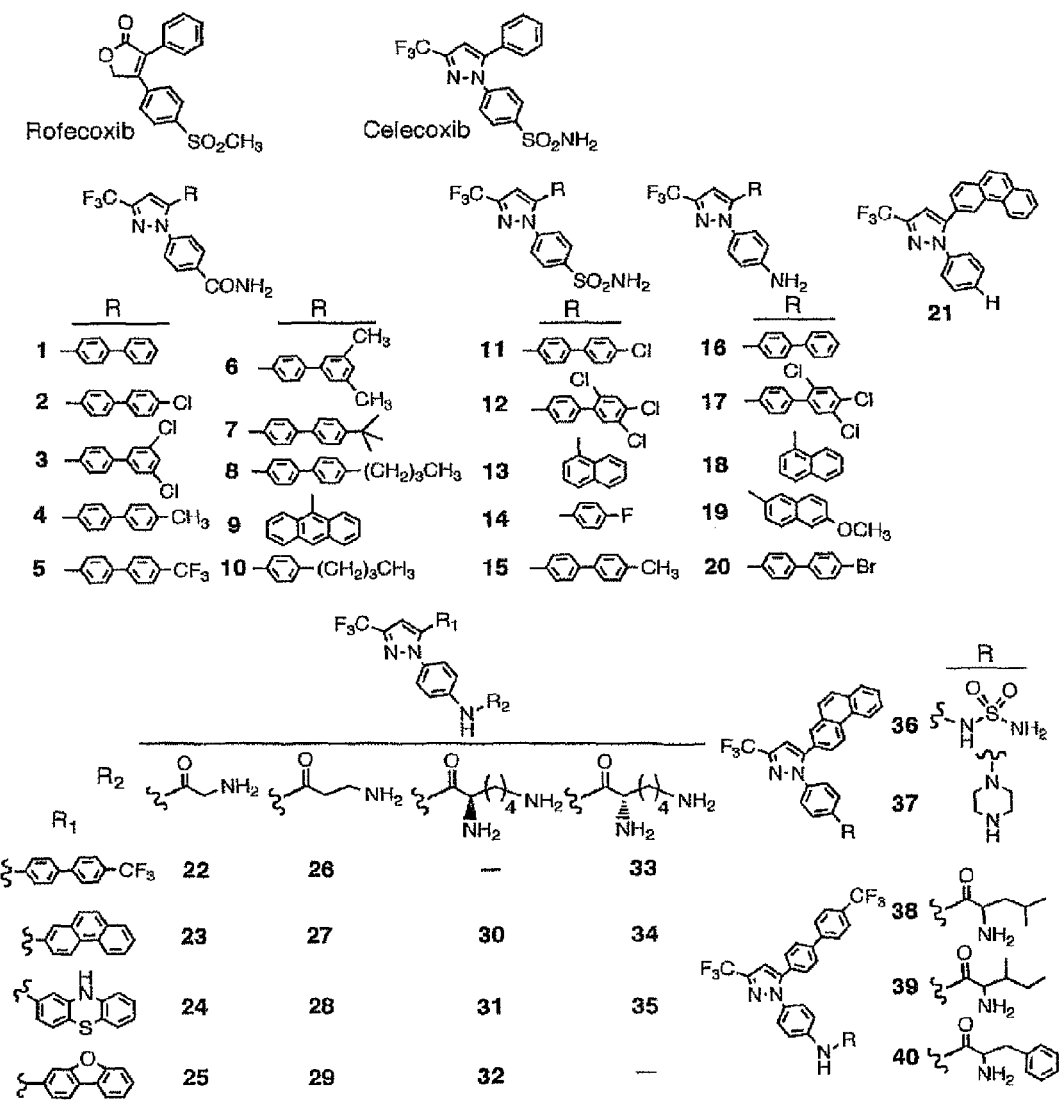
FIG. 2 provides a scheme showing the structures of rofexocib, celecoxib, and compounds 1-40 in the celecoxib-based focused compound library.

The inventors screened a celecoxib-based focused compound library to identify candidate anti-*Staphylococcus* agents for lead optimization (FIG. 1A). Previously, during the course of lead optimization of celecoxib to develop novel PDK-1 inhibitors, the inventors generated a series of derivatives with varying degrees of antiproliferative potency against cancer cells. Zhu et al., J. Natl. Cancer Inst., 94, 1745-1757 (2002). Of these derivatives, 40 representative celecoxib derivatives were chosen for screening against *S. aureus* and *S. epidermidis* (1-40; FIG. 2), which are noteworthy because they represent the most common causes of medical device-associated infections. This screening identified compound 36 as the lead anti-*Staphylococcus* agent, followed by compound 9. Further structural modifications of 36 by substituting the phenanthrene ring with various aromatic structures yielded 41-47, of which compound 46 was identified as the optimal agent. General procedures for the synthesis of compounds 1-47 are depicted in FIG. 1B.

Differential Suppressive Effects of Celecoxib and Rofecoxib on the Growth of *Staphylococcus* Bacteria The inventors examined the suppressive effect of celecoxib on the growth of *S. aureus* (ATCC 29213), *S. epidermidis* (ATCC 35984), and two different strains of MRSA (ATCC 33592 and SCCmec VT), as shown in Table IX. Celecoxib exhibited a clear, though modest, activity against these staphylococcal bacteria with the minimum inhibitory concentrations (MIC) of 32 µg/ml for *S. aureus* and both strains of MRSA, and 16 µg/ml for *S. epidermidis*. Exposure of *S. aureus* to celecoxib at the MIC of 32 µg/ml after 24 h resulted in a 6-log decrease in CFU relative to that of control (data not shown). In contrast, none of these antibacterial activities was noted with rofecoxib (structure, FIG. 1A), even at 64 µg/ml, despite its higher COX-2 inhibitory potency, suggesting that celecoxib's anti-*Staphylococcus* activity is independent of its effects on COX-2.

TABLE IX

MIC's of celecoxib and rofecoxib

| Staphylococcus | MIC$^a$ (µg/ml) | |
|---|---|---|
| | Celecoxib | Rofecoxib |
| S. aureus (ATCC 29213) | 32 | NE |
| S. epidermidis (ATCC 35984) | 16 | NE |
| MRSA (ATCC 33592) | 32 | NE |
| MRSA (SCCmec V$_T$) | 32 | NE |

$^a$NE, no effect of the test agent at 64 µg/ml

Identification of Novel Anti-*Staphylococcus* Agents

The dissociation of these two pharmacological activities (antibacterial versus anti-COX-2) provided a molecular basis for the pharmacological exploitation of celecoxib to develop novel anti-*Staphylococcus* agents. As the target for celecoxib's anti-*Staphylococcus* activity remained unknown, the inventors used an in-house, celecoxib-based focused compound library consisting of 40 derivatives with modifications to the terminal aromatic group (R) and polar side chain (FIG. 2), which were screened for growth inhibitory activities against *S. aureus* (ATCC 29213) and *S. epidermidis* (ATCC 35984). Of these derivatives, compounds 1-8 and 10 of the carboxamide series, 12-15 of the sulfonamide series, 16-20 of the amine series, 21, 22, 32, and 37-40 did not exhibit appreciable activity at 64 µg/ml or improved activity relative to celecoxib (data not shown). However, other derivatives exhibited multi-fold increases in anti-*Staphylococcus* potency (Table X), providing a proof-of-concept of the premise that celecoxib could be structurally modified to enhance its anti-*Staphylococcus* activity. Among these more active derivatives, compound 36, followed by compound 9, represented the lead agents with MIC values of ≤2 µg/ml against both *S. aureus* and *S. epidermidis*.

TABLE X

Anti-*Staphylococcus* (MIC) versus antiproliferative (IC$_{50}$) activities of test agents

| | MIC (µg/ml) | | | |
|---|---|---|---|---|
| Compound | S. aureus (ATCC 29213) | S. epidermidis (ATCC 35984) | IC$_{50}$ (µg/ml) HT-29 cells | Selectivity ratio$^a$ |
| Celecoxib | 32 | 16 | 18 | 0.6 |
| 9 | 2 | 2 | 12 | 6 |
| 11 | 4 | 8 | 12.5 | 3.1 |
| 23 | 4 | 4 | 3.6 | 0.9 |
| 24 | 4 | 4 | 6.2 | 1.6 |
| 25 | 4 | 4 | 6.5 | 1.6 |
| 26 | 4 | 4 | 4.2 | 1.1 |
| 27 | 4 | 4 | 6 | 1.5 |
| 28 | 4 | 4 | 7.5 | 1.9 |
| 29 | 4 | 4 | 7.2 | 1.8 |
| 30 | 4 | 4 | 3.2 | 0.8 |
| 31 | 4 | 4 | 17.5 | 4.4 |
| 33 | 4 | 4 | 3.3 | 0.8 |
| 34 | 2 | 4 | 19.5 | 4.9 |
| 35 | 4 | 4 | 5.2 | 2.6 |
| 36 | 1 | 2 | 12 | 12 |

$^a$Selectivity ratio = IC$_{50}$/MIC against *S. aureus*

Lead Optimization of Compound 36

The above findings underscore the translational potential of compounds 9 and 36 to be developed into potent anti-*Staphylococcus* agents. In addition, lead optimization of 36 was carried out by replacing the phenanthrene ring with different aromatic systems, generating compounds 41-47 (FIG. 1A). These derivatives were assessed for their antibacterial activities against *S. aureus* (ATCC 29213) and *S. epidermidis* (ATCC 35984), which revealed some degree of flexibility in altering the size of the aromatic ring. See Tables XI. For example, the phenanthrene ring could be replaced by biphenyl or substituted biphenyls (42-44) without compromising the anti-*Staphylococcus* activity. Of particular interest is the substitution with an anthracen-9-yl moiety (compound 46), which gave rise to a twofold increase in the anti-*Staphylococcus* potency with MIC of 0.5 µg/ml. Moreover, compound 46 exhibited lower antiproliferative potency against HT-29 cancer cells (IC$_{50}$, 20 µg/ml), providing a selectivity ratio of 40 relative to that of 12 for compound 36. It is noteworthy that compound 46 represents a hybrid of compounds 9 and 36, underlying a subtle structure-activity relationship in interacting with the bacterial target.

TABLE XI

Anti-*Staphylococcus* (MIC) versus antiproliferative (IC$_{50}$) activities of test agents

| | MIC (µg/ml) | | | |
|---|---|---|---|---|
| Compound | S. aureus (ATCC 29213) | S. epidermidis (ATCC 35984) | IC$_{50}$ (µg/ml) HT-29 cells | Selectivity$^a$ ratio |
| 36 | 1 | 2 | 12 | 12 |
| 41 | 4 | 4 | 28 | 7 |
| 42 | 1 | 2 | 16 | 16 |
| 43 | 1 | 2 | 9 | 9 |
| 44 | 1 | 2 | 10 | 10 |
| 45 | 1 | 2 | 19 | 19 |
| 46 | 0.5 | 1 | 20 | 40 |
| 47 | 4 | 4 | 11 | 2.8 |

Discriminative Anti-Growth Activities Against Bacterial Versus Human Cancer Cells.

As celecoxib has been reported to be cytotoxic to cancer cells, the growth inhibitory activities of celecoxib and selected derivatives were assessed in. HT-29 human colon adenocarcinoma cells after 24-h exposure in 10% FBS-supplemented RPMI 1640 medium. As shown in Tables XI and XII, most of the compounds examined suppressed the viability of HT-29 cells with IC$_{50}$ values comparable to their respective MIC values against *S. aureus*, resulting in low selectivity (IC$_{50}$-to-MIC) ratios. It is noteworthy that compounds 36 and 46, the most potent anti-*Staphylococcus* derivatives, showed lower cytotoxic activity against HT-29 cells relative to the other compounds resulting in the highest selectivity ratios (12 and 40, respectively), indicating a better selectivity in suppressing the growth of *Staphylococcus* versus HT-29 cells.

Antibacterial Spectra of Compounds 9, 36, and 41-46 Against Different *Staphylococcus* Species.

As different strains/species of *Staphylococcus* might respond differently to the antibacterial effects of these novel agents, the investigation was expanded to include a panel of representative *Staphylococcus* pathogens, consisting of different strains of *S. aureus, S. epidermidis* and MRSA, as well as *S. haemolyticus, S. hominis, S. intermedius, S. saprophyticus*, and *S. lugdunesis*.

As shown in Table XII, the inhibitory potencies of these test agents against the three strains of MRSA, including the multidrug-resistant community-associated MRSA that carries the novel staphylococcal chromosome cassette mec (SC-Cmec) subtype VT (Boyle-Vavra et al., J. Clin. Microbiol. 43, 4719-4730 (2005), were consistent with those of *S. aureus* and *S. epidermidis*. Among these derivatives, compound 46 represented the optimal anti-MRSA agent with MIC of 0.5 µg/ml, followed by compounds 36 and 42-44, all of which exhibited an MIC value of 1 µg/ml. Moreover, as these MRSA strains have been reported to resist different classes of antibiotics, this finding suggests that a novel antibacterial target is involved in the mechanism of action of these agents.

TABLE XII

Antibacterial spectra of compounds 9 and 36 versus 41-47 against a panel of *Staphylococcus* pathogens

| | MIC (µg/ml) | | | | | | | | |
|---|---|---|---|---|---|---|---|---|---|
| Staphylococcus species | 9 | 36 | 41 | 42 | 43 | 44 | 45 | 46 | 47 |
| Anti-*Staphylococcus* spectra | | | | | | | | | |
| S. aureus (ATCC 29213) | 2 | 1 | 4 | 1 | 1 | 1 | 1 | 0.5 | 4 |
| S. epidermidis (ATCC 35984) | 2 | 2 | 4 | 2 | 2 | 2 | 2 | 1 | 4 |
| S. aureus (ATCC 12598) | 4 | 1 | 4 | 1 | 1 | 1 | 2 | 0.5 | 4 |
| S. epidermidis (ATCC 12228) | 4 | 1 | 4 | 2 | 1 | 1 | 2 | 0.5 | 2 |
| MRSA (ATCC 33592) | 4 | 1 | 4 | 1 | 1 | 1 | 2 | 0.5 | 2 |
| MRSA (SCCmec V$_T$) | 4 | 1 | 4 | 1 | 1 | 1 | 2 | 0.5 | 2 |
| MRSA (ATCC 49476) | 4 | 1 | 4 | 1 | 1 | 1 | 2 | 0.5 | 2 |
| S. haemolyticus (ATCC 29970) | 4 | 2 | 16 | 2 | 2 | 2 | 4 | 2 | 16 |
| S. hominis (ATCC 27844) | 2 | 2 | 8 | 2 | 2 | 2 | 4 | 2 | 2 |
| S. intermedius (ATCC 29663) | 4 | 1 | 8 | 2 | 2 | 2 | 2 | 0.5 | 4 |
| S. saprophyticus (ATCC 15305) | 4 | 2 | 8 | 2 | 2 | 2 | 4 | 2 | 8 |
| S. lugdunesis (NTUH isolate) | 4 | 2 | 16 | 2 | 2 | 2 | 4 | 2 | 4 |

Other non-*Staphylococcus aureus* species examined, with the exception of *S. intermedius*, showed a lesser degree of susceptibility to compounds 36 and 46, with MIC around 2 µg/ml. In contrast, the potency of compound 9 remained relatively unchanged across different *Staphylococcus* species, suggesting subtle differences in the mode of action between the carboxamide (compound 9) and the aminosulfonamides (compounds 36 and 46).

Compounds 36 and 46 are Bactericidal Against MRSA

Figure 3:
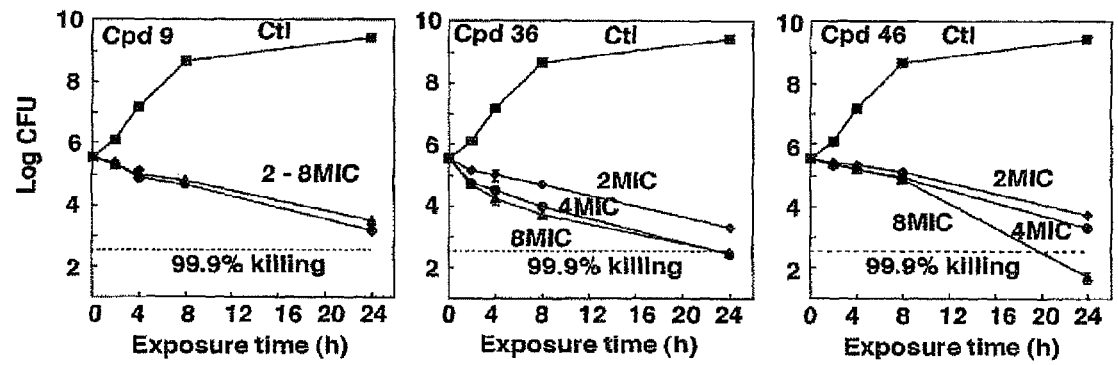
FIG. 3 provides three graphs showing the viability of MRSA ATCC 33592 after exposure to various concentrations (2×, 4×, and 8×MIC) of compound 9 (left panel; MIC, 2 μg/ml), 36 (center panel; MIC, 1 μg/ml), and 46 (right panel; MIC, 0.5 μg/ml) for 2, 4, 8 and 24 h in CAMHB. Numbers of viable bacteria in the broth after each exposure period were enumerated by CFU assay, and the results expressed as CFU/ml. Points indicate means, and bars indicate SD (n=3). The dashed line represents 99.9% cell killing. Ctl, control.
Figure 4:
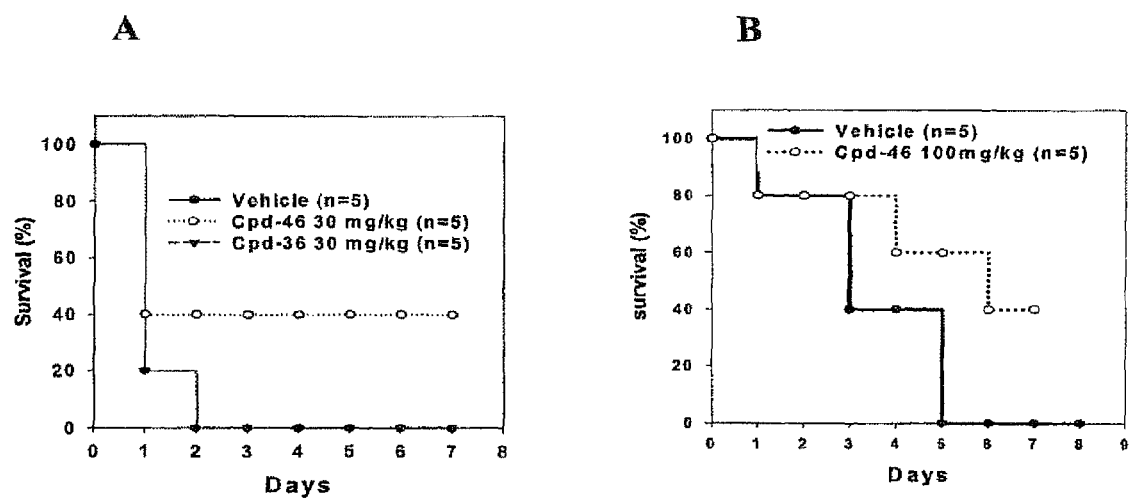
FIG. 4 provides two graphs showing the effect of intraperitoneal and oral administration of 46 improve the survival in methicillin-resistant Staphylococcus aureus-infected mice. (A) Effect of intraperitoneal administration of Cpd-36 and Cpd-46 on survival of methicillin-resistant Staphylococcus aureus-infected mice. C57BL/6 mice were inoculated intraperitoneally with $5 \times 10^7$ CFU of MRSA 33592. At 1 h postinfection, mice were treated intraperitoneally once with vehicle, Cpd-36 or Cpd-46 at 30 mg/kg (B) Effect of oral administration of Cpd-46 on survival of MRSA 33592-infected mice. One hour after intraperitoneal inoculation with $5 \times 10^7$ CFU of MRSA 33592, C57BL/6 mice were treated orally once with Cpd-46 at 100 mg/kg or vehicle. Survival data are presented as Kaplan-Meier survival curves for each treatment group (n=5). The difference in the mean survival times of the groups was statistically significant at P values of 0.05.

An antibacterial agent is defined as bactericidal when it exhibits the distinctive endpoint of causing a 99.9% reduction in bacterial inoculum within a 24-h period of exposure. Otherwise, it is considered bacteriostatic. Pankey, G. A.; Sabath, L. D. Clin. Infect. Dis., 38, 864-870 (2004). To category these novel agents, represented by compounds 9, 36, and 46, in this regard, their time-killing kinetics were assessed in MRSA ATCC 33592 over a 24-h treatment period. Overnight-grown bacteria were inoculated in cation-adjusted Muller Hinton broth (CAMHB) at a concentration of 5×10$^5$ CFU/ml followed by exposure to individual compounds at 2- to 8-fold their respective MIC values. As shown in FIG. 3, compounds 9, 36, and 46 caused time-dependent killing of MRSA, achieving reductions in CFU of 99.14%, 99.91%, and 99.99% respectively, after 24-h exposure to 8 times the MIC. Accordingly, compounds 36 and 46 were classified as bactericidal. As the killing was time-dependent, the antibacterial effect of these agents was not caused by the disruption of membrane integrity. Moreover, in contrast to compounds 36 and 46, compound 9 did not show a dose-dependent effect, in the range of 2×-8×MIC, on cell killing, suggesting a saturation effect in ligand-target interactions. FIG. 4 shows the effect of intraperitoneal and oral administration of compounds 36 and 46 on the survival of methicillin-resistant *Staphylococcus aureus*-infected mice.

Compounds 36 and 46 demonstrated excellent minimum inhibitory concentrations for inhibiting the growth of various strains of *S. aureus* as compared to various other well known antibiotics, as shown in Table XIII.

TABLE XIII

Comparison of the MICs of Cpd-36 and 46 with other clinical using antibiotics

| | Ampicillin | Kanamycia | Streptomycin | Tetracycline | Chloramphenicol | Cpd-36 | Cpd-46 |
|---|---|---|---|---|---|---|---|
| S. aureus (ATCC29213) | 32 | 8 | 16 | 1 | 8 | 1 | 0.5 |
| S. aureus (ATCC33592) | >64 | >64 | >64 | >64 | 64 | 1 | 0.5 |
| S. aureus (SSCmecVT) | >64 | >64 | >64 | 16 | >64 | 1 | 0.5 |
| S. epidermidis (ATCC35984) | 64 | >64 | >64 | 1 | 8 | 2 | 1 |

Discussion

Although hospitals have fought MRSA infections since the late 1960s, the past two decades have witnessed severe community-associated MRSA cases affecting healthy, young individuals with no link to the healthcare system. To date, S. aureus has developed various mechanisms to evade the inhibitory effect of almost all classes of antibiotics, as well as the third-line agent vancomycin. Consequently, MRSA represents an impending public health crisis, and there is an urgent need to develop new anti-MRSA agents with distinct modes of antibacterial action to overcome the multi-drug resistance. Herein the pharmacological exploitation of the "off-target" effect of the COX-2 inhibitor celecoxib on suppressing the growth of Staphylococcus bacteria is described to develop a novel class of anti-MRSA agents with high potency.

Three different strains of MRSA were studied, all of which exhibit resistance to multiple antibiotics, including oxacillin, clindamycin, sulfonamides, erythromycin, tetracycline, cotrimoxazole, gentamicin, chloramphenicol, and streptomycin. Despite this multi-drug resistant phenotype, all of the MRSA strains were as sensitive to the inhibitory effects of compounds 46, 36, and 9 as the methicillin-sensitive S. aureus strains, with MIC values in the range of 0.5 to 2 µg/ml. This lack of cross-resistance suggests that the mode of action of these compounds is different from those of existing antibiotics.

Among the forty-seven derivatives examined, there exists a subtle structure-activity relationship in inhibiting the growth of Staphylococcus bacteria. Although the majority of the compounds of the carboxamide (1-8, 10), sulfonamide (12-15), and amine (16-20) series did not show improved activity over celecoxib (MIC, 32 µg/ml), conversion of any of these three functional groups into an aminosulfonamide moiety increased the anti-Staphylococcus potency by multifold, i.e., 1 and 16 versus 42, 4 and 15 versus 43, 20 versus 44, and 9 versus 46.

The antibacterial target of these compounds is under investigation. Previously, the inventors demonstrated that celecoxib mediated the antiproliferative effect in cancer cells by targeting a number of non-COX enzymes, including certain signaling kinases, such as PDK-1 and CDKs, and endoplasmic reticulum $Ca^{2+}$-ATPases. Through BLASTP analysis, the inventors have identified a number of bacterial proteins of S. aureus and S. epidermidis with some degree of homology to PDK-1 and endoplasmic reticulum calcium ATPases, including a serine/threonine kinase (NP_764450), the copper transporter ATPase copA, potassium transporter ATPase subunit B, and cadmium transporting ATPase. Evaluation of the involvement of these putative targets in the anti-Staphylococcus effects of compounds 9, 36, and 46, in conjunction with genomic analysis of drug-resistant mutants, is currently underway. From a translational perspective, understanding the mode of action of these novel agents will help foster new strategies for the treatment of staphylococcal infections.

Experimental Section

Bacteria. S. aureus strains ATCC 29213, ATCC 12598, MRSA strains ATCC 33592, ATCC 49476, and a clinically isolated MRSA strain carrying SCCmec VT, S. epidermidis strains ATCC 35984 and ATCC 12228, S. haemolyticus strain ATCC 29970, S. hominis strain ATCC 27844, S. intermedius strain ATCC 29663, S. saprophyticus strain ATCC 15305, and a clinically isolated S. lugdunesis were used in this study.

Reagents. Celecoxib was prepared from Celebrex® capsules (Amerisource Health, Malvern, Pa.) by solvent extraction followed by recrystallization from a mixture of ethyl acetate and hexane. Rofecoxib was synthesized according procedures described previously. Prasit et al., Bioorg. Med. Chem. Lett., 9, 1773-1778 (1999).

Unless otherwise indicated, all anhydrous solvents were commercially obtained and stored in Sure-seal bottles under nitrogen. All other reagents and solvents were purchased as the highest grade available and used without further purification. Flash column chromatography was performed with silica gel (Sorbent Technologies, 230-400 mesh). Nuclear magnetic resonance spectra (1H NMR) were measured on a Bruker DPX 300 model spectrometer. Chemical shifts (δ) were reported in parts per million (ppm) relative to the TMS peak. Coupling constants (J) were reported in hertz throughout. Electrospray ionization mass spectrometry analyses were performed with a Micromass Q-T of II high-resolution electrospray mass spectrometer. The purity of all tested compounds was determined to be greater than 95% by elemental analyses, which were performed by Atlantic Microlab, Inc. (Norcross, Ga.) and were reported within 0.4% of calculated values.

The sulfonamide series compounds 11-15, the amine series compounds 16-20, and the amino acid series compounds 22-35 and 38-40 were synthesized as previously described. Zhu et al., J. Natl. Cancer Inst., 94, 1745-1757 (2002); Zhu et al., Cancer Res., 64, 4309-4318 (2004). Syntheses of the active compounds of the carboxamide series (i.e., 9) and the aminosulfonamide series (i.e., 36 and 41-47) are illustrated by the syntheses of compounds 9 and 36, respectively, as examples.

Step a. To a suspension of ethyl trifluoroacetate (1.2 eq.) and NaH (1.25 eq.) in anhydrous THF, individual ketone substrates (1 eq.) in anhydrous THF were slowly added at 25° C. The resulting mixture was stirred for 5 h, concentrated, diluted with ethyl acetate, washed, in tandem, with water, 1N HCl and brine. The organic phase was dried, filtered and concentrated. The residue was purified by flash column chromatography to afford pure 1,3-diketone in fair to good yields.

Step b. A mixture of the 1,3-diketone from step a (1 eq.), individual hydrazaine substrates (1.25 eq.), and concentrated HCl (1.5 eq.) in ethyl alcohol was refluxed until the reaction complete (monitored with TLC). The resulting mixture was concentrated, diluted with ethyl acetate, and washed with water and brine. The organic phase was dried, filtered and concentrated. The residue was purified by flash column chromatography to yield pure pyrazole ring derivatives.

Step c. 4-(5-Anthracen-9-yl-3-trifluoromethyl-pyrazol-1-yl)-benzamide (9). To a solution of 4-(5-anthracen-9-yl-3-trifluoromethyl-pyrazol-1-yl)-benzonitrile generated from step b (0.5 mmol) in DMSO (1 mL) were added $Na_2CO_3$ (1 mmol) and $H_2O_2$ (30%, 0.2 mL) at 0° C. The reaction mixture was stirred at 20° C. for 3 h, and water (3 mL) was added. The white precipitate was filtered, washed with water, and dried to afford compound 9 as off-white crystal in 82% yield. 1H NMR (DMSO-d6) δ 7.16 (s, 1H), 7.19 (s, 1H), 7.34 (br s, 1H), 7.41 (s, 1H), 7.57-7.53 (m, 8H), 7.79 (br s, 1H), 8.17 (m 2H), 8.83 (s, 1H). HRMS exact mass of $C_{25}H_{16}F_3N_3O$, $(M+Na)^+$, 454.1143 amu; found 454.1136 amu. Anal. calcd C 69.60, H 3.74, N 9.74; found C 69.42, H 3.85, N 9.84.

Step d. A reaction mixture of various 5-aryl-1-(4-nitrophenyl)-3-(trifluoromethyl)-1H-pyrazole derivatives (3 mmol), generated from step b, platinum oxide ($PtO_2$, 0.1 mmol) in EtOH was stirred overnight under $H_2$ atmosphere, filtered, and washed with ethyl acetate. The combined filtrate was concentrated and the residue was purified with flash column chromatography to give the corresponding amines with quantitative yields.

N-[4-(5-Phenanthren-2-yl-3-trifluoromethyl-pyrazol-1-yl)-phenyl]-aminosulfonamide (36). Chlorosulfonyl isocyanate (1 mmol) was added dropwise to an ice-cold solution of t-BuOH (1 mmol) in $CH_2Cl_2$, which was then added to a mixture of 4-(5-phenanthren-2-yl-3-trifluoromethyl-pyrazol-1-yl)-phenylamine (1 mmol), generated from step d, and triethylamine (1.5 mmol) in $CH_2Cl_2$. The reaction mixture was stirred at 25° C. for 1 h, and concentrated. The residue was treated with 20% trifluoroacetic acid in $CH_2Cl_2$ for 3 h, washed with 10% $NaHCO_3$, dried, and concentrated. The residue was purified by flash column chromatograph to give 36 as off-white solid in 78% yield. 1H NMR (DMSO-d6) δ 7.35-7.15 (m, 7H), 7.46 (dd, J=1.8, 8.7 Hz, 1H), 7.73-7.65 (m, 2H), 7.88 (dd, J=9, 33.6 Hz, 2H), 8.00-8.05 (m, 1H), 8.09 (d, J=1.8 Hz, 2H), 8.82 (m 2H), 9.89 (br s, 1H). HRMS exact mass of $C_{24}H_{17}F_3N_4O_2S$, $(M+Na)^+$. 505.0922 amu; found: 505.0902 amu. Anal. calcd C 59.75, H 3.55, N 11.61; found C 59,98, H 3.71, N 11.51.

N-[4-(5-p-Tolyl-3-trifluoromethyl-pyrazol-1-yl)-phenyl]-aminosulfonamide (41). 1H NMR ($CDCl_3$) δ 2.30 (s, 3H), 7.27-7.11 (m, 11H), 9.88 (br s, 1H). HRMS exact mass of $C_{17}H_{15}F_3N_4O_2S$, $(M+Na)^+$, 419.0766 amu; found: 419.0755 amu. Anal. calcd C 51.51, H 3.81, N 14.13; found: C 51.30, H 3.79, N 14.08.

N-[4-(5-Biphenyl-4-yl-3-trifluoromethyl-pyrazol-1-yl)-phenyl]-aminosulfonamide (42). 1H NMR ($CD_3OD$) δ 6.96 (s, 1H), 7.25-7.41 (m, 5H), 7.44-7.51 (m, 4H), 7.60-7.63 (m, 4H). HRMS exact mass of $C_{22}H_{17}F_3N_4O_2S$, $(M+Na)^+$, 481.0922 amu; found: 481.0913 amu. Anal. calcd C 57.64, H 3.74, N 12.22; found: C 57.69, H 3.78, N 12.16.

N-{4-[5-(4'-Methylbiphenyl-4-yl)-3-trifluoromethyl-pyrazol-1-yl]-phenyl}-aminosulfonamide (43). 1H NMR ($CD_3OD$) δ 2.37 (s, 3H), 6.95 (s, 1H), 7.35-7.24 (m, 8H), 7.52 (d, J=7.8 Hz, 2H), 7.61 (d, J=8.1 Hz, 2H). HRMS exact mass of $C_{23}H_{19}F_3N_4O_2S$, $(M+Na)^+$, 495.1079 amu; found: 495.1061 amu. Anal. calcd C 58.47, H 4.05, N 11.86; found: C 58.28, H 4.06, N 11.84.

N-{4-[5-(4'-Bromobiphenyl-4-yl)-3-trifluoromethyl-pyrazol-1-yl]-phenyl}-aminosulfonamide (44). 1H NMR (DMSO-d6) δ 7.18-7.49 (m, 1H), 7.68-7.22 (m, 4H), 9.93 (s, 1H). HRMS exact mass of $C_{22}H_{16}BrF_3N_4O_2S$, $(M+Na)^+$, 559.0027 amu; found: 559.0038 amu. Anal. calcd C 49.17, H 3.00, N 10.43; found: C 49.31, H 3.14, N 10.18.

N-[4-(5-Naphthalen-2-yl-3-trifluoromethyl-pyrazol-1-yl)-phenyl]-aminosulfonamide (45). 1H NMR ($CDCl_3$) δ 5.02 (s, 2H), 6.83 (s, 1H), 7.09-7.18 (m, 4H), 7.26 (d, J=6.6 Hz, 2H), 7.49-7.51 (m, 2H), 7.72-7.78 (m, 4H). HRMS exact mass of $C_{20}H_{15}F_3N_4O_2S$, $(M+Na)^+$, 455.0766 amu; found: 455.0753 amu. Anal. calcd C 55.55, H 3.50, N 12.96; found: C 55.34, H 3.52, N 12.69.

N-[4-(5-Anthracen-9-yl-3-trifluoromethyl-pyrazol-1-yl)-phenyl]-aminosulfonamide (46). 1H NMR ($CD_3OD$) δ 6.83 (d, J=8.1 Hz, 2H), 6.99 (s, 1H), 7.06 (d, J=8.4 Hz, 2H), 7.48 (s, 4H), 7.56 (s, 2H), 8.06 (d, J=6.0 Hz, 2H), 8.61 (s, 1H). HRMS exact mass of $C_{24}H_{17}F_3N_4O_2S$, $(M+Na)^+$, 505.0922 amu; found: 505.0905 amu. Anal. calcd C 59.75, H 3.55, N 11.61; found: C 59.89, H 3.66, N 11.52.

N-[4-(5-Anthracen-2-yl-3-trifluoromethyl-pyrazol-1-yl)-phenyl]-aminosulfonamide (47). 1H NMR ($CD_3OD$) δ 7.03 (s, 1H), 7.39-7.16 (m, 8H), 7.48 (s, 2H), 7.98 (s, 2H), 8.38 (d, J=9.6 Hz, 1H). HRMS exact mass of $C_{24}H_{17}F_3N_4O_2S$, $(M+Na)^+$, 505.0922 amu; found: 505.0930 amu. Anal. calcd C 59.75, H 3.55, N 11.61; found: C 59.93, H 3.59, N 11.68.

Antibacterial assays. The MIC of each agent was determined following the guidelines for the broth microdilution method recommended by the Clinical and Laboratory Standards Institute. Wikler, M. A. Performance Standards for Antimicrobial Susceptibility Testing; Eighteenth Informational Supplement Clinical and Laboratory Standards Institute: 2008. Briefly, bacteria grown overnight on Luria Bertani (LB) agar plates were suspended in phosphate-buffered saline (PBS) to an O.D. of 1.0 at 600 nm, which was equivalent to $2\times10^9$ CFU/ml, and then diluted in CAMHB to a final concentration of $5\times10^5$ CFU/ml. The bacterial suspensions were exposed to the test agents and chloramphenicol at escalating doses, ranging from 0.25 to 64 µg/ml, in triplicate in 96-well plates, and the plates were incubated at 37° C. for 24 h. The MIC of each agent was defined as the lowest concentration at which no growth of bacteria was observed.

Antiproliferative assay. The cytotoxicity of individual test agents in HT-29 human colon adenocarcinoma cells was evaluated by using the 3-(4,5-dimethylthiazol-2-yl)-2,5-diphenyltetrazolium (MTT) assay. Briefly, HT-29 cells were seeded into 96-well plates at $1\times10^4$ cells/well (with a minimum of 6 wells per test condition) in RPMI 1640 medium supplemented with 10% FBS and 10 µg/ml of gentamicin. After overnight incubation at 37° C. under 5% CO2, the medium from each well was removed and replenished with fresh aliquots of the same medium containing various concentrations of test agents dissolved in DMSO (final concentration, 0.1%). Control cells were treated with DMSO alone at a concentration equal to that in drug-treated cells. After 24 h of drug exposure, the medium was removed and replaced by 100 µl of 0.5 mg/ml MTT in 10% FBS-containing medium, and the cells were incubated in the $CO_2$ incubator at 37° C. for 2 h. Subsequently, medium was removed from each well, and the reduced MTT dye was dissolved with 100 µl of DMSO per well. Absorbance at 570 nm was measured with a plate reader. The 50% inhibitory concentration ($IC_{50}$) of each drug was determined from dose-response curves by using CalcuSyn software (Biosoft, Cambridge, United Kingdom).

Time-kill assay. To analyze the kinetics of bacterial cell killing, MRSA ATCC 33592 cells at a density of $5\times10^5$ CFU/ml were treated with test agents at 2-, 4-, and 8-fold MICs in triplicate in 24-well plates. Bacterial survival in medium containing DMSO at a concentration equal to that used for drug-treated bacteria served as control. At different times after the start of drug exposure, a 100 µl aliquot of the bacterial suspension was taken from each well and serially diluted with PBS. The diluted samples were spread onto LB agar plates followed by incubation at 37° C. for 16 h. The bacterial colonies on each plate were enumerated, and the number of viable bacteria in each well was expressed as CFU per milliliter.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the celecoxib derivatives are effective, the inventors are not bound by theories described herein. The invention is not limited to the exact details shown and described, for variations obvious to one skilled in the art will be included within the invention defined by the claims.

What is claimed is:

1. A method of treating infection by *Staphylococcus* in a subject, comprising administering to the subject a pharmaceutical composition including a compound of formula I or a pharmaceutically acceptable salt thereof:

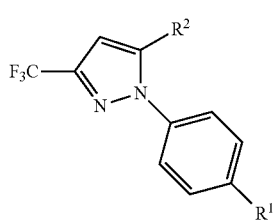

wherein $R^1$ is selected from carboxamide, sulfonamide, amino, aminosulfonamide, and acylamido groups, and $R^2$ is selected from aryl, aralkyl, fused aryl groups, and fused heteroaryl groups.

2. The method of claim 1, wherein $R^1$ is carboxamide and $R^2$ is:

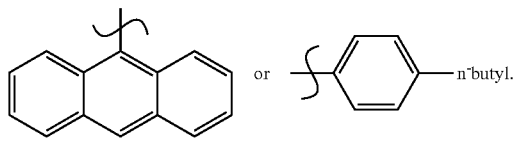

3. The method of claim 2, wherein the compound of formula I has the structure:

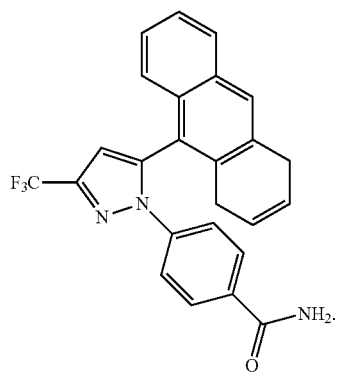 [SMILES: NC(=O)c1ccc(-n2nc(C(F)(F)F)cc2-c2c3c(cc4ccccc24)CC=CC3)cc1]

4. The method of claim 1, wherein $R^1$ is sulfonamide and $R^2$ is selected from the group consisting of:

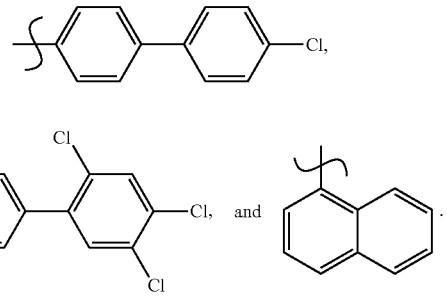

5. The method of claim 1, wherein $R^1$ is acylamido and $R^2$ is selected from the group consisting of:

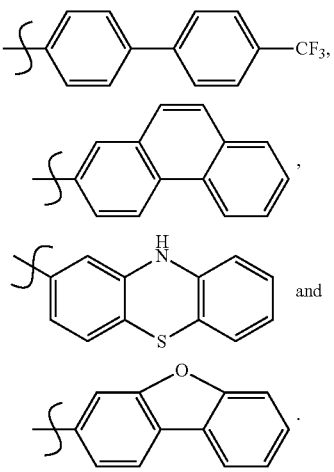

6. The method of claim 5, wherein the acylamido is an amine substituted acylamido having the structure —NH—CO—$(CH_2)_x$—$NH_2$, wherein x is an integer from 1-4.

7. The method of claim 1, wherein $R^1$ is aminosulfonamide, and $R^2$ is a phenyl, biphenyl, naphthyl, or anthracenyl group.

8. The method of claim 7, wherein the compound of formula I has the structure

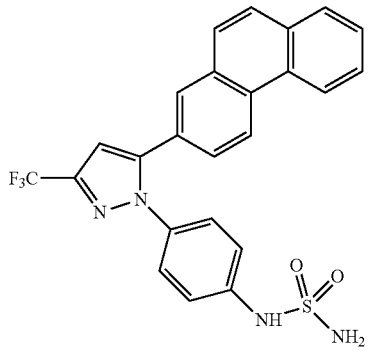

-continued
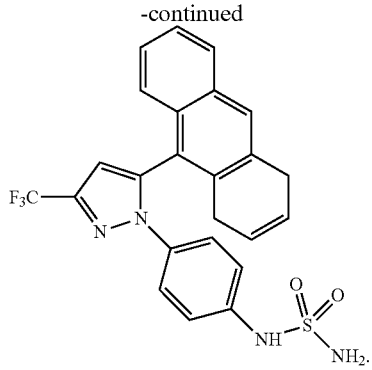
9. The method of claim 1, wherein the *Staphylococcus* is methicillin-resistant.
10. The method of claim 1, wherein the *Staphylococcus* is *Staphylococcus aureus*.
11. The method of claim 10, wherein the *Staphylococcus aureus* is methicillin-resistant.
* * * * *